United States Patent [19]

Lin

[11] 4,013,695

[45] Mar. 22, 1977

[54] 4,4,5,5-TETRADEHYDRO-PGE$_1$ ANALOGS

[75] Inventor: Chiu-Hong Lin, Portage, Mich.

[73] Assignee: The Upjohn Company, Kalamazoo, Mich.

[22] Filed: Oct. 2, 1975

[21] Appl. No.: 619,077

[52] U.S. Cl. .................. 260/410.9 R; 260/211 R; 260/247.2 R; 260/268 R; 260/293.65; 260/326.2; 260/408; 260/413; 260/429.9; 260/439 R; 260/448 R; 260/448.8 R; 260/468 D; 260/473 A; 260/501.1; 260/501.15; 260/501.17; 260/501.2; 260/514 D; 260/520 B; 260/613 D; 260/617 F; 260/624 R; 424/305; 424/308; 424/317; 424/318; 536/18

[51] Int. Cl.$^2$ ........................................ C07C 177/00

[58] Field of Search .......... 260/468 D, 514 D, 408, 260/410.9 R, 413

[56] References Cited

UNITED STATES PATENTS 3,933,889  1/1970  Magerlin ..................... 260/468

*Primary Examiner*—Robert Gerstl
*Attorney, Agent, or Firm*—Robert A. Armitage

[57] ABSTRACT

This invention comprises certain analogs of the prostaglandins in which there is a triple bond between C-5 and C-6 or C-4 and C-5. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

32 Claims, No Drawings

4,4,5,5-TETRADEHYDRO-PGE₁ ANALOGS

BACKGROUND OF THE INVENTION

This invention provides novel compositions of matter. This invention further provides novel processes for producing these compositions of matter.

Particularly this invention provides novel analogs of some of the known prostaglandins which differ from corresponding known prostaglandins in that these prostaglandin analogs have a triple bond between the C-5 and C-6 or C-4 and C-5 positions.

The known prostaglandins include the PGE compounds, e.g. prostaglandin $E_1$ ($PGE_1$) and prostaglandin in $E_2$ ($PGE_2$).

The known prostaglandins include $PGF_\alpha$ compounds, e.g. prostaglandin $F_{1\alpha}$ ($PGF_{1\alpha}$) and prostaglandin $F_{2\alpha}$ ($PGF_{2\alpha}$).

The known prostaglandins include PGA compounds, e.g. prostaglandin $A_1$ ($PGA_1$) and prostaglandin $A_2$ ($PGA_2$).

Each of the above mentioned known prostaglandins (PG's) is a derivative of prostanoic acid which has the following structure and carbon atom numbering

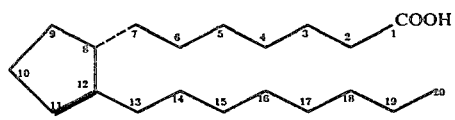

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

$PGE_1$ has the following structure:

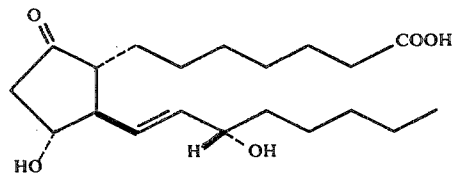

$PGE_2$ has the following structure:

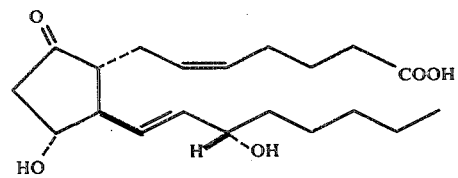

$PGF_{1\alpha}$ has the following structure:

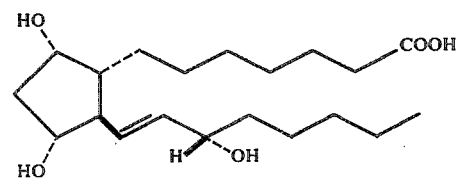

$PGF_{2\alpha}$ has the following structure:

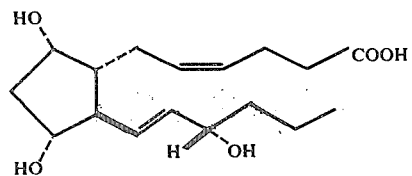

$PGA_1$ has the following structure:

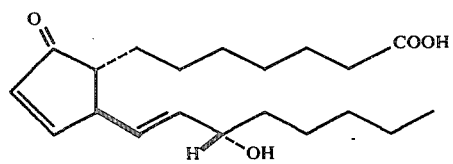

$PGA_2$ has the following structure:

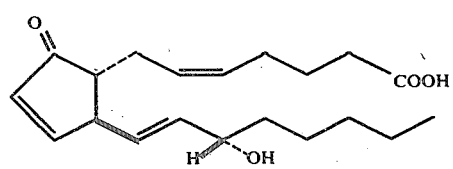

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (∼) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-5, C-6, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the destrorotatory and levorotatory forms. As drawn, the above formulas each represent the particular optically active form of the prostaglandin as is obtained from mammalian tissues, for example, sheep vasicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or "PG" will mean the optically active form of that prostaglandin thereby referred to with the same absolute configuration as $PGE_1$ obtained from mammalian tissues. When reference to the racemic form of one of those prostaglandins in intended, the word "racemic" or "dl" will precede the prostaglandin name.

The term "prostaglandin-type" (PG-type) product, as used herein, refers to any cyclopentane derivative which is useful for at least one of the same pharmacological purposes as the prostaglandins, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparing a prostaglandin-type product each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type product.

The term "prostaglandin analog", as used herein, represents that stereoisomer of a prostaglandin-type product which is of the same relative stereochemical configuration as a corresponding prostaglandin obtained from mammalian tissues or a mixture comprising that stereoiosmer and the enantiomer thereof. In particular, where a formula is used to depict a prostaglandin-type compound herein, the term prostaglandin analog refers to the compound of that formula, or a mixture comprising that compound and the enantiomer thereof.

The various PG's named above, their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein.

For the PGE compounds these biological responses include:

a. stimulating smooth muscle (as shown by tests, for example, on guinea pig ileum, rabbit duodenum, or gerbil colon);

b. effecting lipolytic activity (as shown by antagonism of epinephrine induced release of glycerol from isolated rat fat pads);

c. inhibiting gastric secretion and reducing undesirable gastrointestinal effects from systematic administration of prostaglandin synthetase inhibitors;

d. controlling spasm and facilitating breathing in asthmatic conditions;

e. decongesting nasal passages;

f. decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);

g. affecting the reproductive organs of mammals as labor inducers, abortifacients, cervical dilators, regulators of the estrus, and regulators of the menstrual cycle; and h. accelerating growth of epidermal cells and keratin in animals.

For the $PGF_\alpha$ compound these biological responses include:

a. stimulating smooth muscle (as shown by tests on guinea pig ileum, rabbit duodenum, or gerbil colon);

b. inhibiting gastric secretion and reducing undesirable gastrointestinal effects from systematic administratio of prostaglandin synthetase inhibitors;

c. decongesting nasal passages;

d. decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and e. affecting the reproductive organs of mammals as labor inducers, abortifacients, cervical dilators, regulators of the estrus, and regulators of the menstrual cycle.

For the PGA compounds these biological responses include:

a. stimulating smooth muscle (as shown by tests on guinea pig ileum, rabbit duodenum, or gerbil colon);

b. inhibiting gastric secretion and reducing undesirable gastrointestinal effects from systematic administration of prostaglandin synthetase inhibitors:

c. controlling spasm and facilitating breathing in asthmatic conditions;

d. decongesting nasal passages; and e. increasing kidney blood flow.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anit-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally. Further, the prostaglandin can be conveniently administered orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the from of suppositories; parenterally; subcutaneously; or intramuscularly; with intravenous administration being preferred in emergency situations; by inhalation in the form of aerosols or slutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The prostaglandins so cited above as useful in mammals, including man, as nasal decongestants are used for this purpose. in a dose range of about 10 µg. to about 10 mg. per ml. of a pharmacologically suitable liquid vehicle or as an aerosol spray, both for topical application.

The prostaglandins so cited above as useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually on in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandins so cited above as useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range 0.01 mg. to about 20 mg. per kg. of body weight of the female mammal, advantageously during a span of time starting approximately at the time ov ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for examle, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg. per ml. of the prostaglandin. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in combination at the usual concentration suitable for its use alone.

Prostanoic acid derivatives wherein a triple bond is present between the C-5 and C-6 positions are known in the art. See, for example, Axen, U. F., Chemical Communications: 602 (1970) wherein racemic 5,6,17,18-tetradehydro-15α- or 15α-PGE$_3$, methyl ester is disclosed. See also Ferdinandi, E. S., et al., Canadian Journal of Chemistry 49:1070 (1970) wherein 5,6-didehydro-8α,β-PGE$_2$ or PGB$_2$, methyl ester and 5,6-didehydro-8α,β-15β-PGE$_2$, methyl ester are disclosed. For an additional disclosure of certain 5,6-didehydro prostanoic acid derivatives see Netherlands Pat. No. 3,208,955 (Derwent Farmdoc CPI No. 03130U-B); U.S. Pat. No. 3,773,795 (Derwent Farmdoc CPI No. 73720U-B); Netherlands Pat. No. 7,118,204 (Derwent Farmdoc CPI No. 46347T-B); Belgian Pat. No. 766,009 (Derwent Farmdoc CPI No. (59095S-B); Belgian Pat. No. 747,348 (Derwent Farmdoc CPI No. 67438R-B) and German Offenlegungsschrift No. 2,154,309 (Derwent Farmdoc CPI No. 31279T-B).

SUMMARY OF THE INVENTION

This invention provides novel prostaglandin analogs, esters of these analogs, and pharmacologically acceptable salts of these analogs.

This invention further provides lower alkanoates of these analogs.

This invention further provides novel processes for preparing these analogs.

In particular, this invention comprises: a prostaglandin analog of the formula

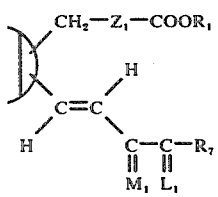

wherein ⟩ is

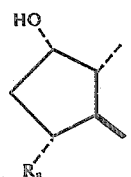

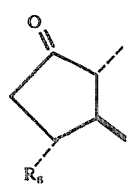

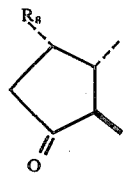

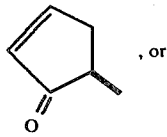

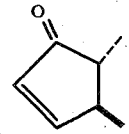

wherein R$_8$ is hydrogen or hydroxy; wherein g is one, 2, or 3; wherein M$_1$ is

or

wherein R$_5$ is hydrogen or methyl;
wherein Z$_1$ is —C≡C—CH$_2$—(CH$_2$)$_g$—CH$_2$— or —CH$_2$—C≡C—(CH$_2$)$_g$—CH$_2$—;
wherein R$_7$ 1. —(CH$_2$)$_m$—CH$_3$, (2) 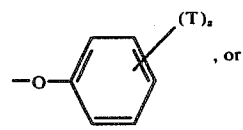, or (3) 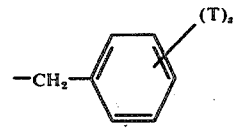

wherein m is one to 5, inclusive T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that R$_7$ is

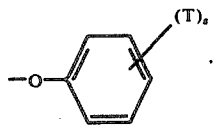

wherein T and s are as defined above, only when R$_3$ and R$_4$ are hydrogen or methyl, being the same or different; wherein L$_1$ is

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmcologically acceptable cation; with the further provisos that:

(1) ⟩ is

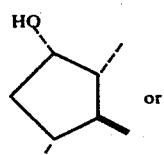 or

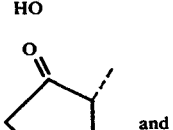 and $R_7$ is —$(CH_2)_m$—$CH_3$, only when $Z_1$ is —$CH_2$—C ≡ C—$(CH_2)_g$—$CH_2$—; and (2) ⟩ is

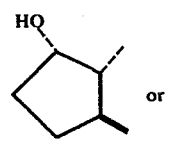 or

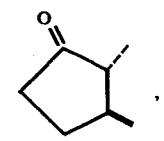, $R_3$, $R_4$, and $R_5$ are all hydrogen, and $R_7$ is —$(CH_2)_m$—$CH_3$, only when $Z_1$ is —$CH_2$—C ≡ C—$(CH_2)_g$—$CH_2$—;

(3) ⟩ is

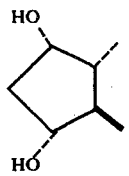,

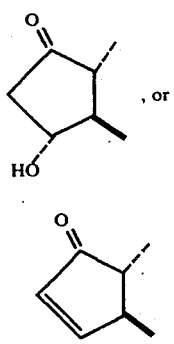, or and $R_7$ is

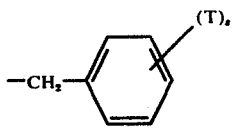

only when $Z_1$ is —$CH_2$—C ≡ C—$(CH_2)_g$—$CH_2$—.

Within the scope of the novel prostaglandin analogs of this invention, there are represented above;

a. PGE-type compounds when the cyclopentane moiety is:

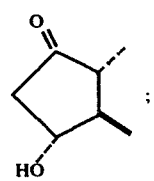;

b. $PGF_\alpha$ -type compounds when the cyclopentane moiety is:

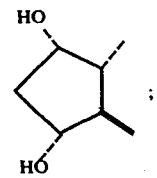;

c. PGD-type compounds when the cyclopentane moiety is:

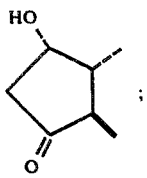

d. 9-deoxy-PGD-type compounds when the cyclopentane moiety is:

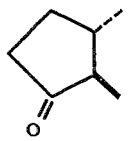

e. 9-deoxy-9,10-didehydro-PGD-type compounds when the cyclopentane moiety is:

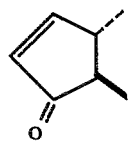

f. 11-deoxy-PGE-type compounds when the cyclopentane moiety is:

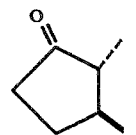

g. 11-deoxy-PGF$_\alpha$ -type compounds when the cyclopentane moiety is:

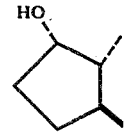

and h. PGA-type compounds when the cyclopentane moiety is:

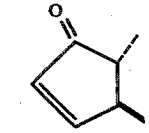

Those prostaglandin analogs herein wherein $Z_1$ is —C≡C—CH$_2$—(CH$_2$)$_g$—CH$_2$— are named as "5,6-dehydro-PG$_2$" compounds. When g is 2 or 3 the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are refered to as C-2a and C-2b, counting from the C-2 to the C-3-position.

When $Z_1$ is —CH$_2$—CH=CH—(CH$_2$)$_g$—CH$_2$—, wherein g is as defined above, the compounds so described are named "4,4,5,5-tetradehydro-PG$_1$" compounds. When g is 2 or 3, the compounds so described are further characterized as "2a-homo" or "2a,2b-dihomo" compounds, respectively, as discussed above.

When $R_7$ is —(CH$_2$)$_m$—CH$_3$, wherein m is as defined above, the compounds so described are named as "19,20-dinor", "20-nor", "20-methyl", or "20-ethyl" compounds when m is one, 2, 4, or 5, respectively.

When $R_7$ is

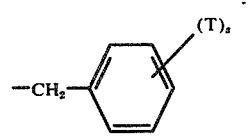

wherein T and s are as defined above, the compounds so described are named as "17-phenyl-18,19,20-trinor" compounds, when s is zero. When s is one, 2, or 3, the corresponding compounds are named as "17-(substituted phenyl)-18,19,20-nor" compounds.

When $R_7$ is

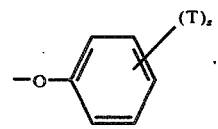

wherein T and s are as defined above, and neither $R_3$, nor $R_4$ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only of $R_3$ and $R_4$ is methyl or both $R_3$ and $R_4$ are methyl, then the corresponding compounds wherein $R_7$ is as defined in this paragraph are named as "16-phenoxy or 16-(substituted pheoxy)-18,19,20-trinor" compounds or "16-methyl-16-phenoxy or 16-(substituted phenoxy)-18,19,20-trinor" compounds, respectively.

When at least one of $R_3$ and $R_4$ is not hydrogen then (except for the 16-phenoxy compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $R_5$ is methyl, the compounds so described are named as "15-methyl" compounds.

For a general description of the nomenclature employed herein see N. A. Nelson, J. Med. Chem. 17, 911 (1974).

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

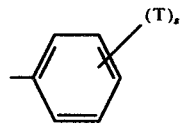

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, p-)-ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-) tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-, m-, or p-trifluoromethylphenyl, (o-, m-, or p-)methoxyphenyl, (o-, m-, p-)ethoxyphenyl, (4- or 5-)chloro-2-methoxyphenyl, and 2,4-dichloro(5- or 6-)methylphenyl.

The novel prostaglandin analogs of this invention correspond to the prostaglandins described above, in that the novel prostaglandin analogs exhibit prostaglandin-like activity.

Specifically the PGE- and 11-deoxy-PGE-type compounds of this invention correspond to the PGE compounds described above, in that these novel PGE- and 11-deoxy-PGE-type compounds are useful for each of the above-described purposes for which the PGE compounds are used, and are used in the same manner as the PGE compounds, as described above.

The PGF$_\alpha$ and 11-deoxy-PGF$_\alpha$ -type compounds of this invention correspond to the PGF$_\alpha$ compounds described above, in that these novel PGF$_\alpha$ and 11-deoxy-PGF$_\alpha$ -type compounds are useful for each of the above-described purposes for which the PGF$_\alpha$ compounds are used, and are used in the same manner as the PGF$_\alpha$ compounds, as described above.

The PGD-, 9-deoxy-PGD-, and 9,10-didehydro-9-deoxy-PGD-type compounds of this invention corresponding to the PGE or PGF$_\alpha$ compounds described above, in that these novel PGD-, 9-deoxy-PGD-, or 9-deoxy-9,10-didehydro-PGD-type compounds are useful for each of the above-described purposes for which either the PGE or PGF$_\alpha$ compounds are used, and are used in the same manner as the PGE or PGF$_\alpha$ compounds, as described above.

The PGA-type compounds of this invention correspond to the PGA compounds described above, in that these novel PGA-type compounds are useful for each of the above described purposes for which the PGA compounds are used, and are used in the same manner as the PGA compounds, as described above.

The prostaglandins described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, shorter, or smaller doses, and make possible self-administration by the patient.

Accordingly, the novel prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For that purpose, it is preferred because of increased water solubility that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The chemical structure of the novel 11-deoxy-PGE-type compounds of this invention renders them less sensitive to dehydration and rearrangement than the corresponding prostaglandins, and these compounds accordingly exhibit a surprising and unexpected stability and duration of shelf life.

The novel PG analogs of this invention are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and staight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, basic amino acid cations or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as hereocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-butylethanolamine, 2-amino-1-butanol, 2-amino-2-ethyl-1,3-Propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Examples of basic amino acids are L-arginine and L-lysine.

The novel PG analogs of this invention used for the purposes described above in free hydroxy form or also in the form wherein the hydroxy moieties are transformed to lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

It is preferred that the carboxy-terminated side chain contain either 7 or 9 carbon atoms, especially preferred that it contain 7, i.e., the natural chain length of the prostaglandins. Further when $R_7$ is $-(CH_2)_m-CH_3$, it is preferred that $m$ be 3. For those compounds wherein $R_7$ is

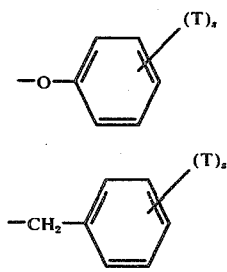

it is preferred that $s$ be zero or one and $T$ be chloro, fluoro, or trifluoromethyl.

For those compounds wherein at least one of $R_3$ and $R_4$ is methyl or fluoro, it is preferred that $R_5$ be hydrogen. For those compounds wherein $R_5$ is methyl, it is preferred that $R_3$ and $R_4$ both be hydrogen. For those compounds wherein $R_7$ is

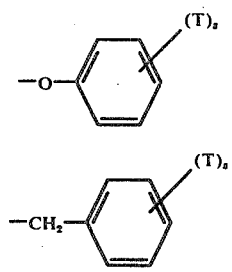

it is preferred that $R_3$, $R_4$, and $R_5$ all be hydrogen.

It is further preferred that the 15-hydroxy not be of the 15-epi configuration, i.e., that the hydroxy be in the alpha configuration when the formulas of the novel PG analogs are as drawn herein.

Especially preferred are those compounds which satisfy two or more of the above preferences. Further, the above preferences are expressly intended to describe the preferred compounds within the scope of any generic formula of novel prostaglandin analogs disclosed herein. Thus, for example the above preferences describe preferred compounds within the scope of each formula of a prostaglandin analog provided in the Tables hereinafter.

In another aspect of the interpretation the preferences herein, the various prostaglandin cyclopentane ring structures as employed herein are each representative of a particular "parent structure" which is useful in naming and categorizing the novel prostaglandin analogs disclosed herein. Further, where a formula depicts a genera of PG analogs disclosed herein evidencing a single cyclopentane ring structure, then each corresponding genus of PG analogs evidencing one of the remaining cyclopentane ring structures cited herein for novel prostaglandin analogs is intended to represent an equally preferred genus of compounds. Thus, for example, for each genus of $PGF_\alpha$ -type products depicted by a formula herein, the corresponding genus of PGD-, PGE-, and 11-deoxy-$PGF_\alpha$ -type products are equally preferred embodiments of the invention as the genera of $PGF_\alpha$ -type products.

Finally where subgeneric grouping of PG analogs of any cyclopentane ring structure are described herein, then the corresponding subgeneric groupings of PG analogs of each of the remaining cyclopentane ring structures are intended to represent equally preferred embodiments of the present invention.

The Charts herein describe methods whereby the novel prostaglandin analogs of this invention are prepared.

With respect to the Charts $R_1$, $R_7$, $M_1$, $L_1$, $Z_1$, and g are as defined above. $M_5$ is

or a mixture of

and

$M_6$ is

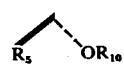

or

Chart A

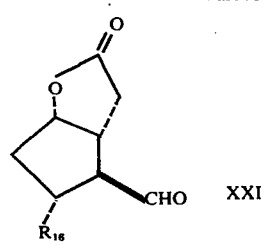

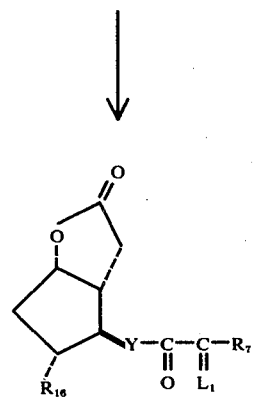

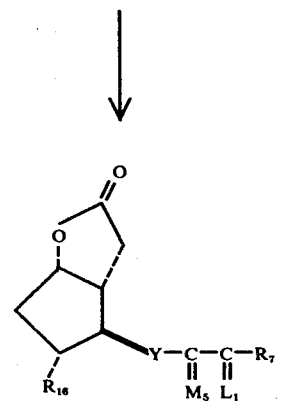

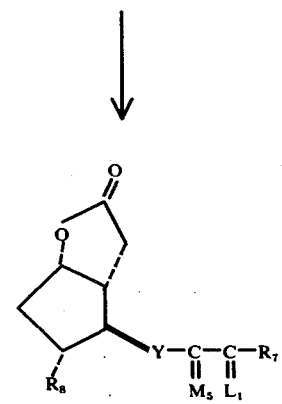

-continued
Chart A
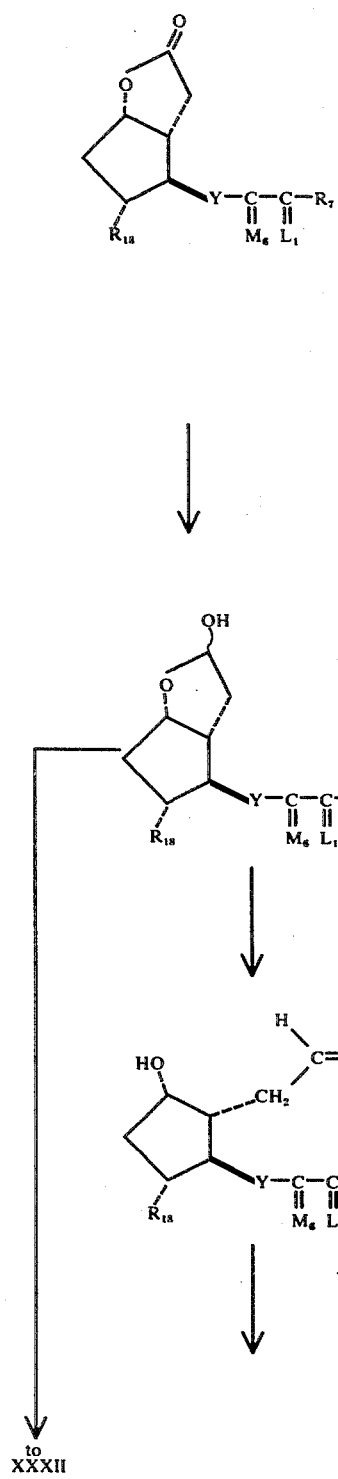
-continued
Chart A
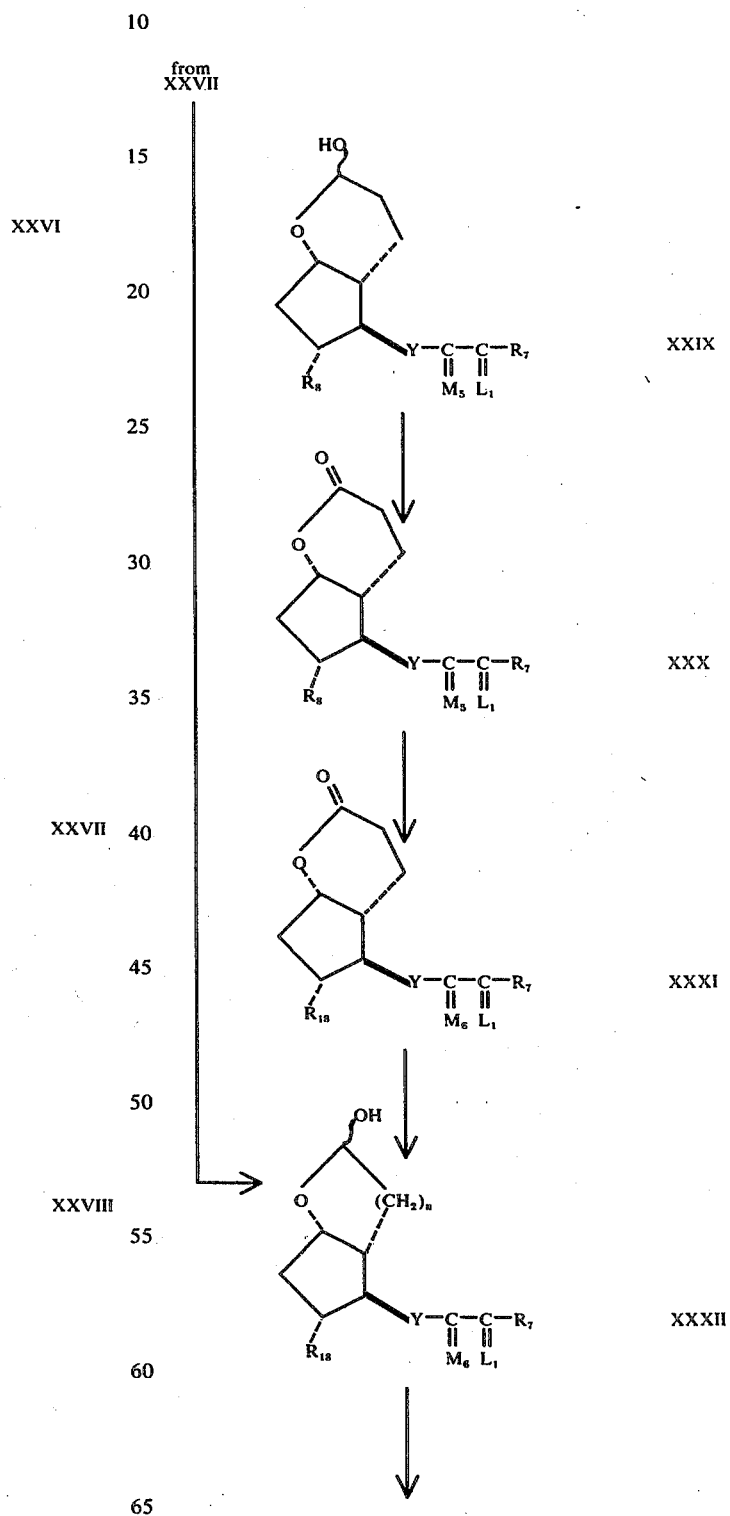

Chart A (continued)
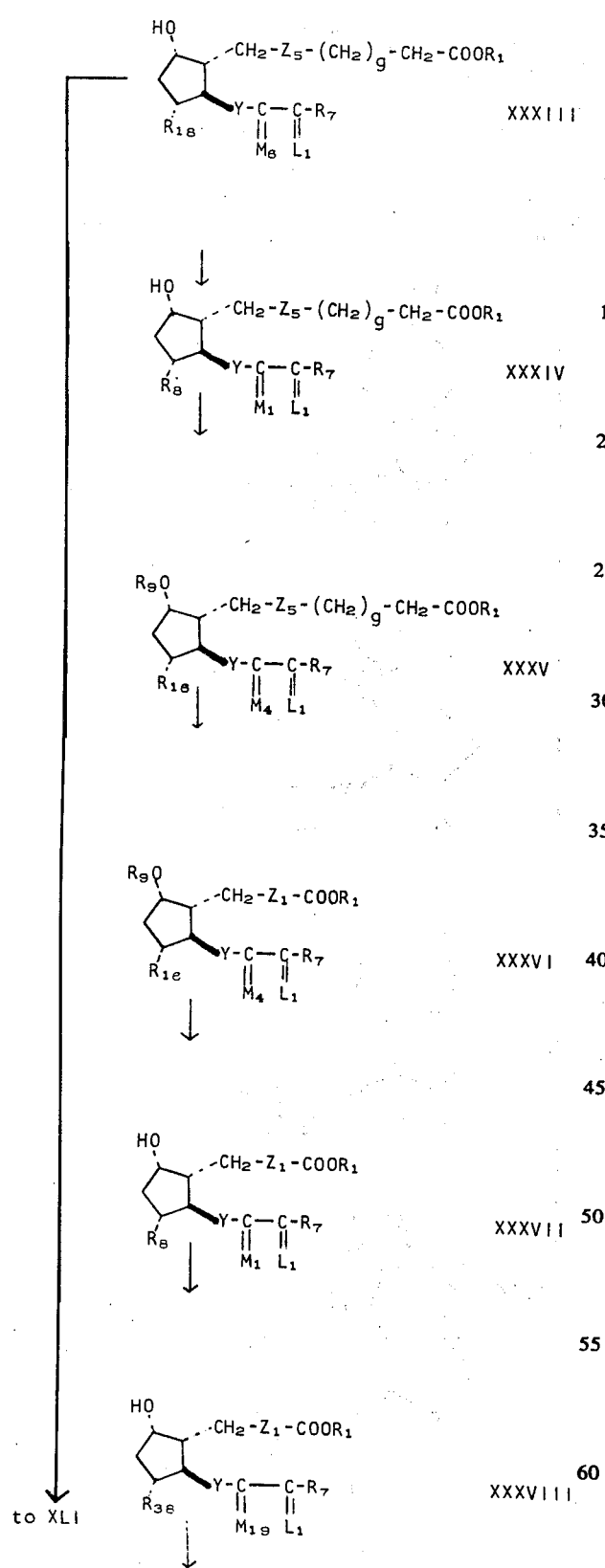
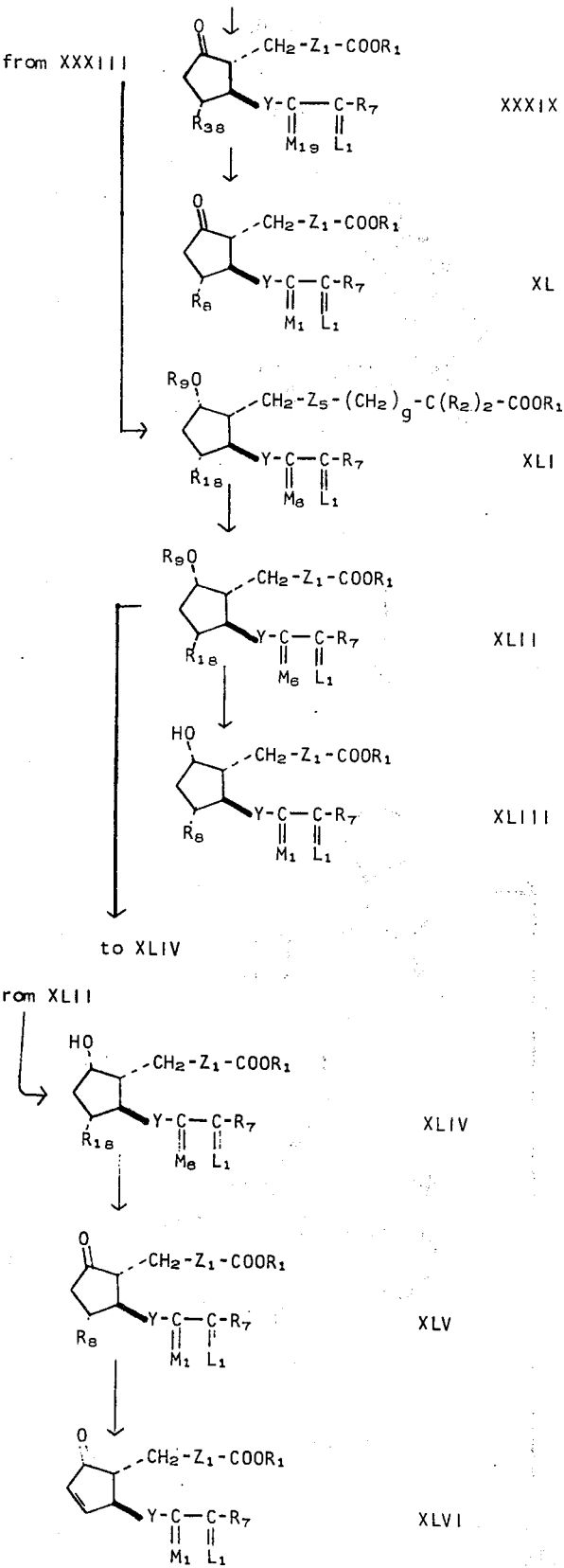

Chart B
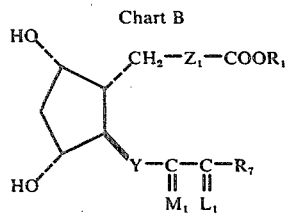 LI
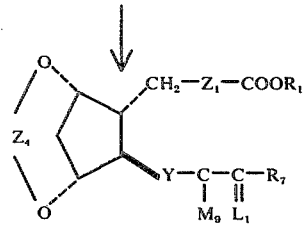 LII
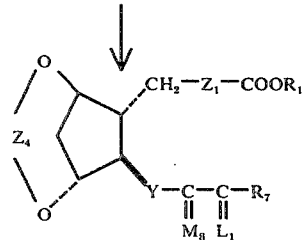 LIII
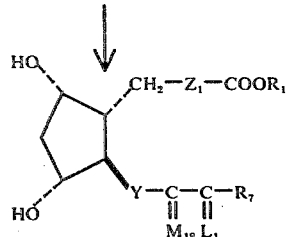 LIV
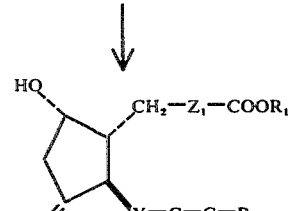 LV
TO LVII
from LV
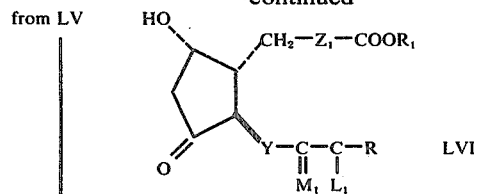 LVI
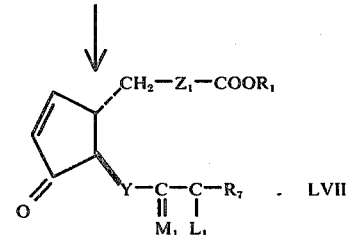 LVII
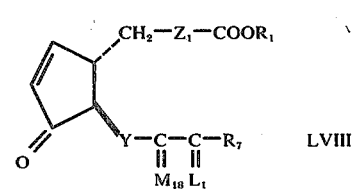 LVIII
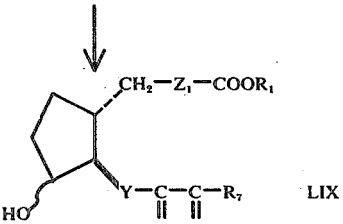 LIX
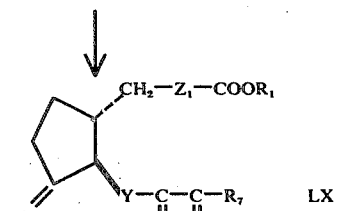 LX
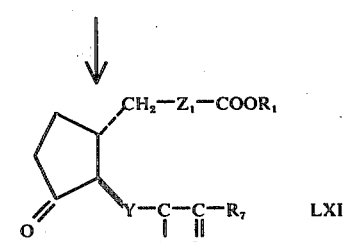 LXI Chart C
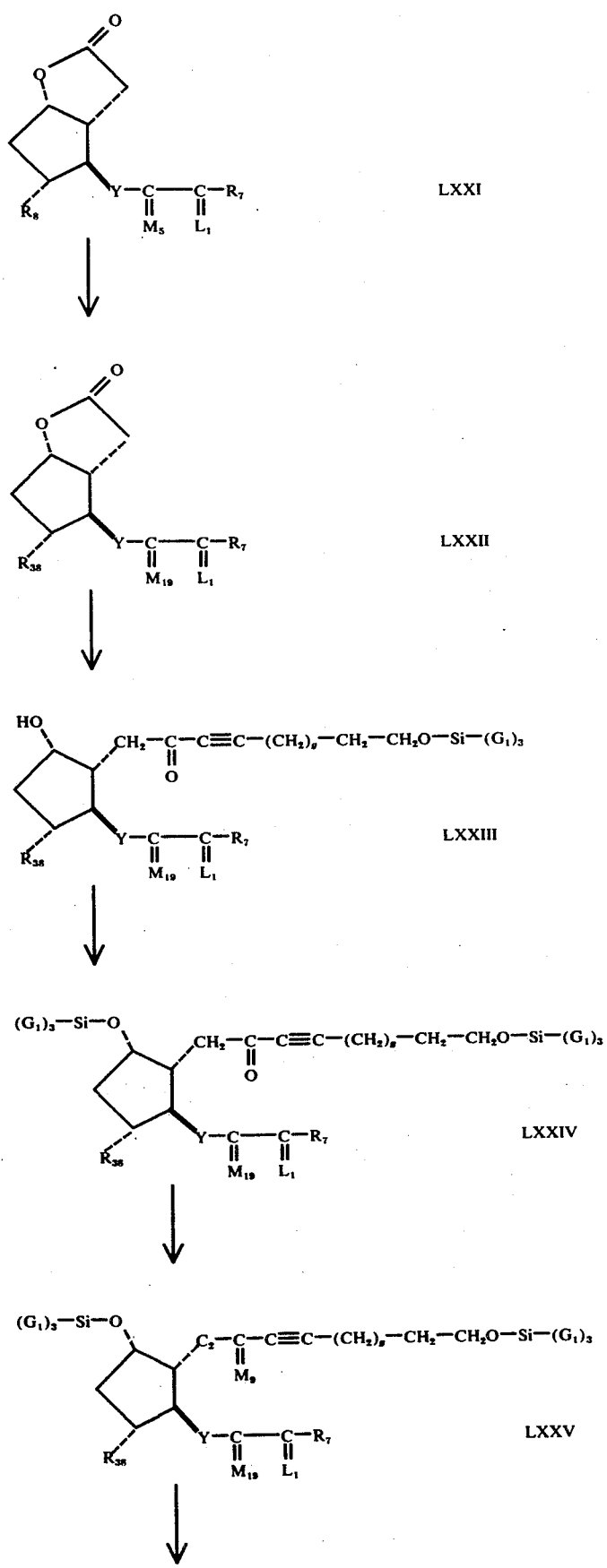
LXXI
LXXII
LXXIII
LXXIV
LXXV -continued
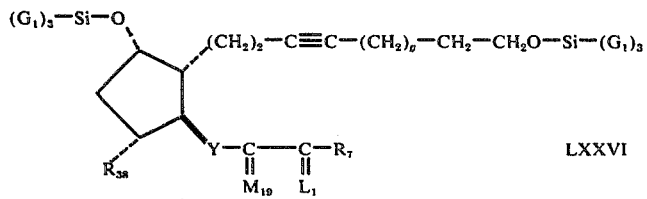
LXXVI
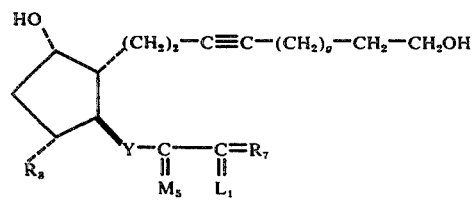
LXXVII
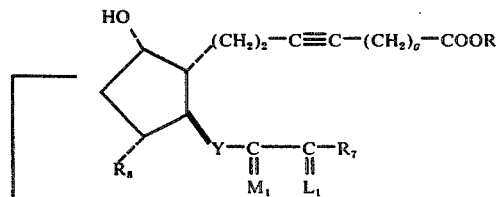
LXXVIII
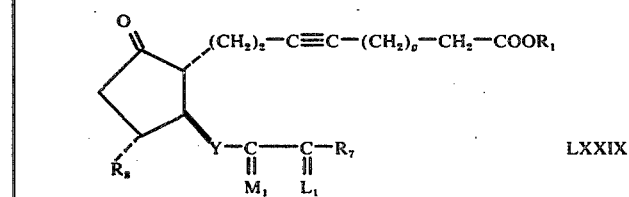
LXXIX
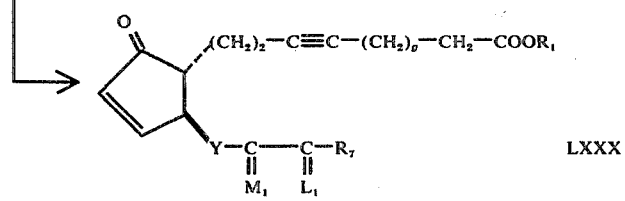
LXXX
or the mixture of epimers thereof, wherein $R_{10}$ is a blocking group and $R_5$ is as defined above. $M_4$ is
or the mixture of epimers thereof, wherein $R_9$ is an acyl protecting group and $R_5$ is as defined above. $M_8$ is
or
wherein $R_{10}$ is a blocking group. $M_9$ is
or -continued $M_{18}$ is

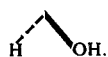

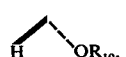

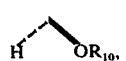

or

wherein $R_{10}$ is a blocking group. $M_{19}$ is

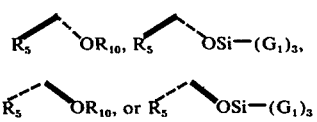

wherein $R_5$, $R_{10}$, and G are as defined herein.

$R_8$ is hydrogen or hydroxy.

$R_{16}$ is hydrogen or $-OR_9$, wherein $R_9$ is an acyl protecting group. $R_{18}$ is hydrogen or $-OR_{10}$, wherein $R_{10}$ is a blocking group. $R_{26}$ is hydrocarbyl, including alkyl, aralkyl, cycloalkyl, and the like. Examples of these hydrocarbyl groups include 2-methylbutyl, isopentyl, heptyl, octyl, nonyl, tridecyl, octadecyl, benzyl, phenethyl, p-methylphenethyl, 1-methyl-3-phenylpropyl, cyclohexyl, phenyl, and p-methylphenyl.

$Z_4$ is $$n\text{-}C_4H_9B\diagup\diagdown$$

and $Z_5$ is cis—CH=CH—CH$_2$ or cis—CH$_2$—CH=CH—. Y is trans- CH=CH—.

$G_1$ is alkyl of one to 4 carbon atoms, aralkyl of 7 to 12 carbon atoms, phenyl, or phenyl substituted with one or 2 fluoro, chloro, or alkyl of one to 4 carbon atoms, with the proviso that in the $-Si-(G_1)_3$ moiety the various $G_1$'s are the same or different. Preferably one of $G_1$ is tert-butyl and the remaining 2 are methyl. $R_{38}$ is hydrogen $-OR_{10}$ or $-OSi-(G_1)_3$.

$R_9$ is an acyl protecting group. Acyl protecting groups according to $R_9$, include:

a. benzoyl;

b. benzoyl substituted with one, to 5 alkyl of one to 4 carbon atoms, inclusive, phenylalkyl of 7 to 10 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;

c. benzoyl substituted with alkoxycarbonyl of 2 to 5 carbon atoms, inclusive;

d. naphthoyl;

e. naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or f. alkanoyl of 2 to 12 carbon atoms, inclusive.

In preparing these acyl derivatives of a hydroxy-containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with hydroxyl-containing compound in the presence of a hydrogen chloride scavenger, e.g. a tertiary amine such as pyridine triethylamine or the like. The reaction is carried out under a variety of conditions, using procedures generally known in the art. Generally mild conditions are employed: 20°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides, (($R_9)_2O$), or acyl chlorides ($R_3Cl$): benzoyl; substituted benzoyl, e.g., 2-, 3-, or 4-(-methylbenzoyl), (2-, 3-, or 4-)-ethylbenzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4 -, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)methyl-1-naphthoyl, (2- or 4-) ethyl-1-naphthoyl, 2-isopropyl-1-naphthoyl, 4,5-dimethyl -1-naphthoyl, 6-isopropyl-4-methyl-1-naphthoyl, 8-benzyl-1-naphthoyl, (3-, 4-, 5-, or 8-) -nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching cite.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor as reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, Proceedings of the Robert A. Welch Foundation Conferences on Chemical Research, 12, Organic Synthesis, pgs. 51–79 (1969). Those blocking groups which have been found useful include a. tetrahydropyranyl;
b. tetrahydrofuranyl; and
c. a group of the formula $$-C(OR_{11})(R_{12})-CH(R_{13})(R_{14}),$$

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or $-(CH_2)_b-O-(CH_2)_c-$, wherein $a$ is 3, 4, or 5, or $b$ is one, 2, or 3, and $c$ is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid of pyridine hydrochloride. The dihydropyran is used in large stoichiometric excess, preferably 4 to 10 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula $$-C(OR_{11})(R_{12})-CH(R_{13})(R_{14}),$$

wherein $R_{11}$, $R_{12}$, $R_{13}$, and $R_{14}$ are as defined above, the appropriate reagent is a vinyl ether, e.g. isobutyl vinyl ether or any vinyl ether of the formula $$C(OR_{11})(R_{12})=C(R_{13})(R_{14}),$$

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

The process steps of Chart A transforming XXI to XXIV are generally known in the art using known reagents and starting materials.

With respect to Chart A the formula XXI compound is known in the art. This compound is available in either optically acitive or racemic form. The formula XXI compound in racemic form may be transformed into corresponding optically active compound by methods known in the art.

The formula XXII compound is prepared from the formula XXI compound by a Wittig alkylation. Reagents known in the art or prepared by methods known in the art are employed. The transenone lactone is obtained stereospecifically. See for reference D. H. Wadsworth, et al., Journal or Organic Chemistry 30, 680 (1965).

In the preparation of the formula XXII compound, certain phosphonates are employed in the Wittig reaction. These phosphonates are of the general formula $$(R_{15}O)_2\overset{O}{\underset{\|}{P}}-CH_2-\overset{O}{\underset{\|}{C}}-\overset{L_1}{\underset{\|}{C}}-R_7$$

wherein $L_1$ and $R_7$ are as defined above and $R_{15}$ is alkyl of 1 to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methylphosphonate as produced using n-butyllithium. For this purpose, acids of the general formula $$HOOC-\overset{L_1}{\underset{\|}{C}}-R_7$$

are employed in the form of their lower alkyl esters, preferably methyl or ethyl. The methyl esters for example are readily obtained by reaction of the corresponding acids with diazomethane.

For example, when $R_7$ is $$-O-\underset{}{\underset{}{\bigcirc}}(T)_s$$

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o-, m-, or p-)ethylphenoxy-, 4-ethyl-o-tolyloxy-, (o-,m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of the $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichlorophenoxy-, (4- or 6)-chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted phenoxy)propionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted phenoxy)propionic acids include those wherein $R_7$ is: phenoxy-, (o-, m-, or p-)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the $(T)_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is benzyl or substituted benzyl.

For example, when $R_3$ and $R_4$ of the $L_1$ moiety are both hydrogen there are available the following phenyl or substituted phenyl propionic acids: (o-, m-, or p-)phenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl there are available, for example, the following 2,2-dimethyl-3-phenyl or substituted phenyl propionic acids: phenyl- and p-methylphenyl.

When one and only one of $R_3$ and $R_4$ is fluoro, there is available, for example, 2-fluoro-3-phenyl propionic acid.

Phenyl substituted acids (as above wherein $R_7$ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted benzyl chloride. Thus, the above acid is obtained by the following reaction:

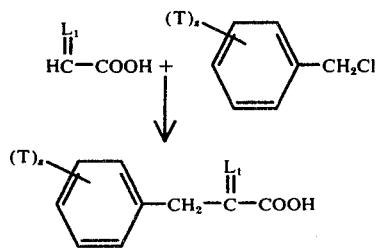

The above reaction proceeds smoothly, ordinarily at 0° C. The produce acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when both $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxoalkanoic acids, i.e. butyric, pentanoic, hexanoic, heptanoic, and octanoic. The transformation of these 2-oxo-alkanoic acids to the corresponding 2,2-difluoro alkanoic acids proceeds by methods known in the art, using known ketonic fluorinating reagents. For example, $M_oF_6.BF_3$ is advantageously employed in the fluorination.

The formula XXIV compound is prepared from the formula XXII 3-oxo bicyclic lactone by transformation of the 3-oxo-moiety to the $M_5$ moiety.

The above 3-oxo bicyclic lactone is transformed to the corresponding 3α- or 3β-hydroxy bicyclic lactone, wherein $M_5$ is

or

by reduction of the 3-oxo moiety, followed by separation of the 3α- and 3β-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium potassium, the zinc borohydrides, lithium(tri-tert-butoxy)-aluminum hydride, metal trialkox-borohydrides, e.g. sodium trimethoxy borohydride, lithium borohydride, and the like. In those case in which carbon-carbon double bond reduction need not be avoided, the boranes, e.g. disiamylborane (bis-3-methyl-2-butyl borane) are alternatively employed.

For the production of C-15 epimerically pure prostagladins, the 15-epi compound is separated from the mixture by methods known in the art. For example, silica gel chromatography is advantageously employed.

The 3-oxo bicyclic lactone is transformed into the corresponding (3RS)-3-methyl bicyclic lactone wherein $M_5$ is a mixture of

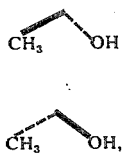

and by reaction of the 3-oxo bicyclic lactone with a Grignard reagent, $CH_3MgHal$, wherein Hal is chloro, bromo, or iodo. The Grignard complex is thereafter hydrolyzed, for example, using saturated aqueous ammonium chloride as is known in the art. An alternate method for transforming the 3-oxo compound to a 3(RS)-3-methyl compound is by reaction of the 3-oxo bicylic lactone with trimethylaluminum.

The preferred method for separation of these (3RS)-3-methyl epimers is by separation of the corresponding C-15 epimers of the PG-type, methyl esters using silica gel chromatography or high pressure liquid chromatography (HPLC).

The formula XXV compound is prepared from the formula XXIV compound by deacylation, as described above. The formula XXVI compound is then prepared from the formula XXV compound by replacing any free hydroxy moieties with blocking groups according to $R_{10}$ by the procedure described above. The formula XXVII compound is then prepared from the formula XXVI compound by reduction of the formula XXVII lactone to a lactol. Methods known in the art are employed. For example, diisobutylaluminum hydride is employed at −70° to −80° C.

Thereafter the formula XXVII compound is transformed to either the formula XXVIII or XXXII compound.

The formula XXVII compound undergoes condensation to form the formula XXVIII enol. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below −10° C. The formula XXVII lactol is mixed with the above reagent and the condensation proceeds smoothly within the temperature range of −30° C.-+30° C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy, isobutoxy-, s-butoxy-, and t-butoxymethylenetriphenylphosphorane. Various hydrocarbyloxymethylenetriphenylphosphoranes which are optionally substituted for the alkoxymethylenetriphenylphosphoranes and are accordingly useful for preparing the formula XXVIII intermediates wherein $R_{23}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346–348, John Wiley and Sons, New York, New York, (1965). The formula XXVIII enol intermediates are then hydrolyzed to the formula XXIX lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXX compound is then prepared from the formula XXIX compound by oxidation of the formula XXIX lactol to a lactone. This transformation is carried out, using for example, silver oxide as an oxidizing reagent, followed by treatment with pyridine hydrochloride.

The formula XXX lactone may then be converted to the formula XXXI ether by transformation of any free hydroxy moieties to blocking groups, according to $R_{10}$, following the procedures herein described for these transformations.

Thereafter the formula XXXII compound (wherein $n$ is 2) is prepared from the formula XXXI compound by reduction of the formula XXXI lactone to a lactol. For example, diisobutylaluminum hydride is employed as is described above for the reduction of lactones to lactols. The formula XXXII lactol is alternately represented by the formula XXVII compound when $n$ is one.

The formula XXXIII compound is prepared from the formula XXXII compound by a Wittig alkylation, using the appropriate (ω-carboxyalkyl)triphenylphosphonium bromide. The reaction proceeds as is generally known in the art, by first mixing the appropriate (ω-carboxyalkyl)-triphenylphosphonium bromide with sodio dimethylsulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXIII cis-4,5-didehydro-$PGF_{1\alpha}$ - or 11-deoxy-$PGF_{1\alpha}$ -, or 11-deoxy-$PGF_{2\alpha}$ -, or $PGF_{2\alpha}$ -type compound.

The formula XXXIII compound is then transformed to the formula XLI compound by acylation or the formula XXXIV compound by hydrolysis of any blocking groups followed by an optional separation of 15-epimers. Such hydrolysis proceeds as described above and such acylation by the methods described above for introducing acyl protecting groups.

The formula XXXIV compound is then prepared from the hydrolyzed formula XXXIII compound by transformation of the $R_1$ moiety of the formula XXXIII compound to its methyl ester. Methods hereinbelow described are employed. The C-15 epimers are then optionally separated, thereby preparing the formula XXXIV compound wherein $R_1$ is methyl.

The formula XXXIV compound is represented by hydrolyzed formula XXXIII when the C-15 moiety consists of separated C-15 epimers.

The formula XXXV compound is then prepared from the formula XXXIV compound by replacing free hydroxy hydrogens with acyl protecting groups, according to $R_9$, following the procedure described above. Thereafter the formula XXXV compound is transformed to the formula XXXVI 5,6-didehydro-$PG_2$-type compound or 4,4,5,5-tetradehydro-$PG_1$-type compound by halogenation (bromination or chlorination) followed by dehydrohalogenation.

The halogenation described above consists of transforming the formula XXXV $PG_2$-type compound to a corresponding 5,6-dihalo-$PG_1$-type compound or transforming the formula XXXV cis-4,5-didehydro-$PGF_{1\alpha}$ -type compound to a corresponding 4,5-dihalo-$PGF_{1\alpha}$ -type compound. This halogenation proceeds by mixture of the molecular halogen (e.g. $Br_2$ or $Cl_2$) with the formula XXXV compound in a diluent which comprises a chlorinated hydrocarbon. Preferred reaction temperatures are between −40° and 0° C. with −20° C. being especially preferred. Chlorinated hydrocarbon intermediates preferred as diluents include carbon tetrachloride, chloroform, and dichloromethane. Thereafter, the formula XXXVI compound is prepared by dehydrohalogenation with base. Amine bases are especially preferred, and in particular 1,5-diazobicyclo[5.4.0.]undecene-5 is preferred. See Fieser and Fieser, Vol. 2, page 101 (1969). Thereafter, the formula XXXVII compound is prepared from the formula XXXVI compound by deacylation, following procedures described hereinabove.

Alternatively, dehydrohalogenation and deacylation are achieved in one step, employing potassium t-butoxide in dimethylsulfoxide.

When the above reactions hydrolyze an ester, the ester moiety is conveniently restored employing esterification methods described below.

Transformations XXXVII to XL provide a method whereby the formula XXXVI $PGF_\alpha$ or 11-deoxy-$PGF_\alpha$ -type compound is transformed into the corresponding PGE- or 11-deoxy-PGE-type compound by selective silylation of all hydroxy hydrogens of the formula XXXVII compound, other than the C-9 hydroxy.

The formula XXXVIII compound is prepared from the formula XXXVII compound by selective silylation of the various hydroxy groups of the formula XXXVII compound over the C-9 hydroxy. Silyl groups with the scope $-Si(G_1)_3$, wherein $G_1$ is alkyl of one to 4 carbon atoms, inclusive, aralkyl of 7 to 12 carbon atoms, inclusive, phenyl, phenyl substituted with one or 2 chloro, fluoro, or alkyl of one to 4 carbon atoms, inclusive, with the proviso that the various $G_1$'s of the $-Si(G_1)_3$ moiety are the same or different, are employed. These reagents are known in the art and their use is known in the art.

For the selective silylation procedure methods known in the art for selective silylation of known prostanoic acid derivatives are employed. See for reference U.S. Pat. No. 3,822,303 (issued July 2, 1974), German Offenlegungschrift No. 2,259,195 (Derwent Farmdoc CPI 36457U-B), and Netherlands Pat. No. 7,214,142 (Derwent Farmdoc CPI 26221U-B).

Examples of the $-Si(G_1)_3$ moiety are trimethylsilyl, dimethyl(tert-butyl)silyl and dimethylphenylsilyl. Examples of alkyl of one to 4 carbon atoms, inclusive, aralkyl of 7 to 12 carbon atoms, inclusive, and phenyl or substituted phenyl moieties are provided hereinabove.

The formula XXXIX compound is prepared from the formula XXXVIII compound by oxidation of the C-9 hydroxy to a C-9 oxo. Oxidation reagents and methods known in the art are employed. For example, the Jones or Collins Reagent is advantageously employed.

The formula XL compound is prepared from the formula XXXIX compound by hydrolysis of the silyl groups. Hydrolysis proceeds by methods known in the art, e.g. the use of water or dilute aqueous acetic acid in a diluent of water and a quantity of a water miscible solvent sufficient to yield a homogeneous reaction mixture. This hydrolysis is ordinarily complete within 2 to 12 hr. at 25° C., and is preferably carried out in an atmosphere of a inert gas such as nitrogen or argon.

As described above the formula XLI compound is prepared by acylation of a C-9 hydroxy of the formula XXXIII compound. Thereafter, the formula XLI compound is transformed to the formula XLII compound following the procedure described above for the preparation of the formula XXXVI compound from the formula XXXV compound.

Thereafter the formula XLIII PGF-type products are prepared by deacylation and hydrolysis of any blocking groups following the methods and procedures described hereinabove. Optionally the formula XLII compound is used to prepare the formula XLIV compound. This preparation proceeds by deacylation employing methods and procedures described above. Thereafter, the formula XLV 11-deoxy-PGE- or PGE-type compound is prepared from the formula XLIV compound by oxidation. Methods and reagents known in the art are employed.

Finally, the formula XLVI compound is prepared from the formula XLV compound wherein $R_8$ is hydroxy by mild acidic dehydration, employing methods known in the art for dehydration of PGE-type compounds to PGA-type compounds or is optionally recovered as a by-product of the transformation of the formula XLIV compound to the formula XLV compound.

In the employment of the processes above when formula XXXIV C-15 tertiary alcohols are to be prepared ($R_5$ is methyl) the use of blocking groups is not required. Accordingly, in the steps of the above charts the introduction and hydrolysis of blocking groups are thereby omitted by the preferred process.

Certain (3RS)-3-methyl lactones of Chart A may be separated into their respective (3S)- or (3R)-epimers by silica gel chromatographic separation techniques. Where such separation is possible, this route is preferred. Accordingly, in these cases the separation is effected and $M_5$ is

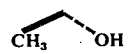

or

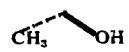

and $M_4$ is

or

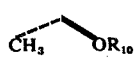

wherein $R_{10}$ is a blocking group. Accordingly, the separation procedure of PG-type intermediates is omitted when the optional lactone separation is employed.

When a formula XXXIV cis-4,5-didehydro-PGF$_{1\alpha}$ - or cis-4,5-didehydro-11-deoxy-PGF$_{1\alpha}$ -type compound is to be prepared by the procedure of Chart A, the Wittig alkylation step XXXII to XXXIII may be performed on the formula XXIX lactol, instead of the formula XXXII lactol, thereby eliminating the oxidation, etherification, and reduction steps of Chart A (XXIX through XXXII).

Chart B provides a method whereby the formula LI PGF$_\alpha$ -type product prepared above is transformed to the corresponding novel formula LVI PGD-type compound of this invention, which is thereafter transformed respectively to the formula LVII 9-deoxy-9,10-didehydro-PGD-type product or formula LXI 9-deoxy-PGD-type product.

The formula LII compound is prepared from the formula LI compound by cyclobutylboronization. Accordingly, the bicyclic formula LII compound is prepared by reaction of the formula LI compound with a slight stoichiometric excess of butylboronic acid. The course of the reaction is conveniently monitored by silica gel thin layer chromatography and the reaction is preferably carried forth under vigorous stirring at reflux temperatures. The preferred reaction diluent for this transformation is methylene chloride, though other suitable organic solvents are likewise employed. The formula LII compound so formed is then etherified by replacing the free hydroxy hydrogen of the $M_9$ moiety with a blocking group according to $R_{10}$. Procedures hereinabove described are advantageously employed. Thereafter the formula LIV compound, which is represented by formula LI when $R_5$ is methyl, is prepared from the formula LIII compound by decycloboronization. For this purpose an alkaline metal hydroxide (e.g., sodium, lithium, or potassium hydroxide) is combined with the formula LIII compound in a water-miscible diluent capable of yielding a homogeneous reaction mixture (e.g., methanol or ethanol), and the resulting solution thereafter treated with dilute aqueous hydrogen peroxide. The formula LV compound is then prepared from the formula LIV compound by one of two methods.

By the first method the formula LIV compound is selectively oxidized at the C-11 over the C-9 position using, for example, the Jones reagent. In order to achieve high selectivity, it is desirable that the reaction be carried out at between −20° and −60° C. Especially preferred are reaction temperatures between −55° and −40° C. Accordingly, upon separation of mixtures of product, the pure formula LV PGD-type compound is obtained.

By the second procedure the formula LV compound is prepared from the formula LIV compound first selectively silylating the C-11 hydroxy of the formula LIv compound over the C-9 hydroxy. Silyl groups according to the formula —Si(G$_1$)$_3$ are advantageously employed. For selective monosilylation procedures see U.S. Pat. No. 3,822,303, issued July 2, 1974, German Offenlegungsschrift No. 2259195, Derwent Farmdoc CPI 36457U-B or Netherlands Pat. No. 7214142, Derwent Farmdoc CPI 26221U-B. Thereafter the silylated compound so formed is transformed to the corresponding C-9 ether, employing blocking groups according to $R_{10}$, in place of the 9-hydroxy hydrogen. Thereafter the C-11 silyl moiety is hydrolyzed by methods herein-above described and the resulting 11-hydroxy compound oxidized by the procedure described above, yielding the corresponding 11-oxo compound. Thereafter, the formula LVI compound is prepared from this 11-oxo compound by replacing any blocking groups according to $R_{10}$ with hydroxy hydrogens. Methods described hereinabove are employed.

Additionally Chart B provides a method whereby formula LV or LVI PGD-type compound is transformed variously into the formula LVII 9-deoxy-9,10-didehydro-PGD-type compound, the formula LXI 9-deoxy-PGD-type compound.

The formula LVII or LVIII compound is prepared, respectively from the formula LV or LVI compound by mild acid catalyzed dehydration of the formula LV or LVI compound. Organic acids such as acetic acid, trifluoroacetic acid, citric acid, oxalic acid, or p-toluenesulfonic acid are useful for this purpose. Diluents such as tetrahydrofuran, methanol, ethanol, or water are usefully employed. Preferably, however, a diluent is employed which will result in a homogeneous reaction mixture. The dehydration proceeds rapidly at temperatures between ambient temperature and 40° C. Alternatively, a formula LV or LVI compound is left standing on a column of acid washed silica gel, thereby dehydrating to the formula LVII or LVIII product, usually within one to 5 days. The formula LIX is thereafter prepared from the LVIII compound by reduction of the formula LVIII compound. This reduction selectively reduces the endocyclic double bond and transforms the 11-oxo to an 11-hydroxy, without affecting side chain unsaturation. For this purpose, an alkali metal borohydride, e.g. sodium, potassium, or lithium borohydride is effectively employed in aqeuous solution. The reaction is carried out at about −20° C. and is ordinarily complete within a few minutes.

The formula LVIII compound is optionally converted into the formula LX compound by selective catalytic hydrogenation of the endocyclic double bond. This transformation is selectively effective without affecting side chain unsaturation. For this purpose the 5 to 10 percent palladium or rhodium catalyst on carbon, alumina, or other suitable support is employed. The reaction is carried out in any suitable organic solvent, e.g. ethyl acetate, methanol, ethanol, or diethyl ether, at temperatures of between −30° and 50° C. and pressures greater than or equal to atmospheric pressure.

Alternatively the formula LX compound is then prepared from the formula LIX compound by oxidation as described above in the transformation of the formula LIV compound to the formula LV compound. For this purpose an oxidizing agent such as the Jones reagent (acidified chromic acid) is employed. See for reference, Journal of the Chemical Society 39 (1946). A sight stoichiometric excess beyond the amount necessary to oxidize the secondary hydroxy group of the formula LIX compound is employed. Acetone is a useful diluent for this purpose. Reaction temperatures at least as low as about 0° C. are useful. Preferred reaction temperatures are in the range of −10° to −50° C. An especially useful reagent for this purpose is the Collins reagent (chromium trioxide in pyridine). See for reference J. C. Collins, et al., Tetrahedron Letters 3363 (1968). Dichloromethane is a suitable diluent for this purpose. Reaction temperature below 30° C. are preferred. Reaction temperatures in the range of about −10° to +10° C. are especially preferred. The oxidation proceeds rapidly and is ordinarily complete within several minutes. Pure product is then isolated by conventional means, e.g. silica gel chromatography.

Examples of other oxidation agents useful for this transformation are silver carbonate on Celite, Chemical Communications, 1102 (1969), mixtures of chromium trioxide in pyridine (Journal of the American Chemical Society 75, 422 (1953)), and tert-butyl chromate in pyridine (Biological Chemistry Journal, 84, 195 (1962)), mixtures of sulfur trioxide in pyridine and dimethyl sulfoxide (Journal of the American Chemical Society 89, 5505 (1967)), and mixtures of dicyclohexylcarbodiimide and dimethylsulfoxide (Journal of the American Chemical Society 87, 5661 (1965)).

Thereafter the formula LXI compound is prepared from the formula LX compound by hydrolysis of blocking groups according to $R_{10}$, as described hereinabove.

Chart C provides a method whereby formula LXXI bicyclic lactone is transformed to the formula LXXVIII 4,4,5,5-tetra-dehydro-PGF$_{1\alpha}$ -type compound of 4,4,5,5-tetradehydro-PGE$_1$-type compound.

The formula LXXI starting material is available in the art or prepared by methods known in the art. For example, Chart A provides a method for the preparation of the formula LXXI compound. See, for example, the preparation of the formula XXV compound therein. Thereafter, the formula LXXII compound is prepared from the formula LXXI compound by silylation. For this purpose it is preferred to use a silyl moiety known to be stable and selectively hydrolyzable. For example, -Si(G$_1$)$_3$ is preferred to be t-butyldimethylsilyl. Optionally, however (and particularly when PGE$_1$-type products are to be prepared) blocking groups according to $R_{10}$ rather than silyl groups are introduced in this transformaton. Accordingly, procedures described in Chart A for transformation of the formula XXV compound of the formula XXVI compound are employed.

Thereafter, the formula LXXIII compound is prepared from the formula LXXII compound by alkyne addition. This alkyne addition proceeds by reacting the appropriate ω-t-butyl dimethylsilyloxy-1-alkyne, HC≡C—(CH$_2$)$_g$—CH$_2$—CH$_2$OSi—(G$_1$)$_3$, with the formula LXXII compound in the presence of an organolithium compound, e.g. methyl lithium. The reaction preferably proceeds at temperatures below 0° C. (about −10° C.) under a nitrogen atmosphere. When the reaction is complete, the reaction mixture is conveniently quenched by addition of ammonium chloride. Thereafter the formula LXXIII compound is transformed to the formula LXXIV compound by silylation. For this purpose it is preferred that the same silyl moiety which appears on the formula LXXII or formula LXXIII compound be introduced. When by the optional procedures described herein the formula LXXII and formula LXXIII compound contain blocking groups in place of silyl moieties, the use of a t-butyldimethylsilyl moiety is preferred. Silylation procedures for the transformations described in this Chart are accomplished by methods known in the art.

Thereafter, the formula LXXV compound is prepared from the formula LXXIV compound by reduction of the formula LXXIV 6-oxo compound to the corresponding 6-hydroxy compound. This reduction is achieved by methods hereinabove described for reduction in the secondary hydroxy moieties (the transformation of the formula LVIII compound or the formula LVIX compound). Accordingly, by a preferred method sodium borohydride is employed as is known in the art.

The formula LXXVI compound is prepared from the formula LXXV compound by removal of the 6-hydroxy. This removal is accomplished first by transforming the 6-hydroxy to a corresponding alkyl-, aralkyl-, or phenyl- or substituted phenyl- sulfonyl derivative (e.g. forming the tosylate or mesylate of the formula LXXV compound) and thereafter reducing the alkyl-, aralkyl-, or phenyl- or substituted phenylsulfonate to the formula LXXVI compound. For accomplishing the sulfonation, the formula LXXV compound in the presence of an amine catalyst (e.g. pyridine) is allowed to react with the appropriate sulfonyl chloride. Accordingly, p-toluenesulfonyl or methylsulfonyl chloride is reacted with the formula LXXV compound in pyridine. When this reaction is complete, the reduction which follows is conveniently accomplished by use of reagents known to replace alkyl, aralkyl, or phenyl sulfonyloxy moieties with hydrogen. Thus, lithium aluminum hydride is conveniently employed. This reduction is conveniently run at room temperature under a nitrogen atmosphere. The reaction temperatures are preferably about 0°–25° C. Thereafter, the formula LXXVI compound is transformed to the formula LXXVII primary alcohol by hydrolysis of the silyl groups. For this purpose methods known in the art are conveniently employed. Thus, for example, a mixture of tetrahydrofuran, water, and acetic or trifluoroacetic acid or trifluoroacetic acid or a mixture of a lower alkanol, water, and acetic acid are employed to hydrolyze various silyl moieties.

When blocking groups according to $R_{10}$ have been employed in the transformation of the formula LXXI compound to the formula LXIII compound, then it is preferred to hydrolyze the 9-silyl moiety by a method which does not effect the 11,15-bis ethers when a PGE-type product is to be prepared. Accordingly, selective hydrolysis of the silyl group proceeds by methods known in the art. See for reference Corey, et al., Journal of the American Chemical Society 94, 6190 (1972). An especially useful reagent for this purpose is tetra-n-butylammonium fluoride in tetrahydrofuran.

Thereafter, the formula LXXVIII compound is prepared from the formula LXXVII compound by oxidation of the primary alcohol to a carboxylic acid, followed by optional transformation of the acid so formed to its $R_1$ derivative and optional separation of any mixed C-15 epimers. The oxidation of the primary alcohol to its corresponding carboxlic acid employs reagents known in the art for such transformations. For example, a hydrogen-reduced aqueous suspension of platinum dioxide (Adams catalyst, Fieser and Fieser, Reagents for Organic Synthesis, N.Y., N.Y., 1977, page 890) is employed advantageously in accomplishing this oxidation. Thereafter, the optional transformations and separation of epimers proceeds by methods herein described.

Thereafter the formula LXXVIII 4,4,5,5-tetradehydro-PGF$_{1\alpha}$ product is transformed to the corresponding formula LXXIX or LXXX 4,4,5,5-tetrahydro-PGE$_1$ or PGA$_1$ product employing the method described in Chart A for the preparation of the formula XLV or XLVI compound form the formula XLIV compound, respectively.

When by the optional procedures of this Chart the formula LXXVII compound (as discussed above) is an 11,15-bis-ether, then the formula LXXIX compound is prepared from the formula LXXVII compound preferably employing a one-step Jones oxidation (employing methods hereinabove discussed), followed by hydrolysis of any blocking groups (following procedures hereinabove described).

Optically active PG-type products are obtained from optically active intermediates, according to the process steps of the above charts. Likewise optically active PG-type compounds are obtained from corresponding optically active PG-type compounds following the procedures in the above charts. When racemic intemediates are used in the reactions above, racemic products are obtained. Finally where intermediates are used as mixtures of enantiomers, mixtures of enantiomers are obtained as final products, as well as diastereomers in some cases. These products may be used in their racemic form, as mixtures of enantiomers, if preferred they may be resolved as optically active enantiomers following procedures known in the art. For example, when a PG-type free acid is obtained, the racemic form thereof is resolved into d and forms by reacting said free acid by known procedures with an optically active base (e.g., brucine or struchnine) thereby yielding a mixture of 2 diastereomers which are separable by procedures known in the art (fractional crystallization to yield the separate diastereomeric salts). The optically active acid may then be prepared from the salt by general procedures known to the art.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to acids ($R_1$ is hydrogen) or to esters.

When the alkyl ester has been obtained and an acid is desired, saponification procedures, as known in the art for PGF-type compounds are employed.

For alkyl esters of PGE-type compounds enzymatic processes for transformation of esters to their acid forms may be used by methods known in the art when saponification procedures would cause dehydration of the prostaglandin analog. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reaction, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tertbutyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid PG-type compounds, differing as to yield and purity of product.

Thus by one method, the PG-type compound is converted to a tertiary amine salt, reacted with pivaloyl halide to give the mixed acid anhydride and then reacted with the aromatic alcohol. Alternatively, instead of pivaloyl halide, an alkyl or arylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John Wiley and Sons, Inc., New York, (1967). The PG-type compound is contacted with one to ten molar equivalents of the aromatic alcohol in the presence of 2–10 molar equivalents of dicyclohexylcarbodiimide in pyridine as a solvent.

One preferred novel process for the preparation of these esters, however, comprises the steps:

a. forming a mixed anhydride with the PG-type compound and isobutylchloroformate in the presence of a tertiary amine and b. reacting the anhydride with an appropriate aromatic alcohol.

The mixed anhydride described above is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the PG-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form an crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, or hexanoic anhydride gives the corresponding carboxyacylate.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent.

An inert organic diluent, (eg., dioxane) can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24 hour reaction time is used.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are in degrees centigrade.

IR (Infrared) absorption spectra are recorded on a Perkin-Elmer Model 421 Infrared spectrophotometer. Except when specified otherwise, undiluted (neat) samples are used. UV (Ultraviolet) spectra are recorded on a Cary Model 15 spectrophotometer.

NMR (Nuclear Magnetic Resonance) spectra are recorded on a Varian A-60, A-60D, T-60 spectrophotometer on deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol, Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas Hoover melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

EXAMPLE 1

Dimethyl 3,3-dimethyl-2-oxo-4-phenylbutylphosphonate,

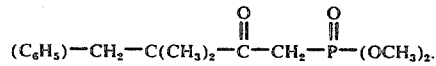

A. To a solution of 101.2 g. of diisopropylamine in 125 ml. of tetrahydrofuran under nitrogen at 0° C. is added dropwise with cooling (using an ice-methanol bath) 625 ml. of n-butyllithium in hexane. To the resulting solution is added dropwise with cooling 46.5 ml. of isobutyric acid. This mixture is then stirred at 0° C. for 90 min. and thereafter cooled to −15° C. Benzyl chloride (60 ml.) is added with stirring at such a rate as to maintain the reaction temperature below −5° C. The resulting mixture is thereafter stirred at ambient temperature for 4 hr. This stirred mixture is then diluted with diethyl ether and excess cold dilute hydrochloric acid. The organic layer is washed with saline and thereafter dried, concentrated, and the residue distilled under vacuum. Accordingly, there is prepared 2,2-dimethyl-3-phenyl propionic acid.

B. A mixture of 48 g. of the product of part A of this example and 82 g. of thionyl chloride are heated with stirring on a steam bath for 2 hr. The mixture is then concentrated under vacuum. Thereafter dry benzene is added and the resulting mixture is concentrated again, removing all traces of thionyl chloride. Distillation of this residue yields 48.2 g. of 2,2-dimethyl-3-phenylpropionyl chloride.

C. To a solution of 63 g. of dimethylmethylphosphonate in 600 ml. of tetrahydrofuran under nitrogen at −75° C. is added with stirring 312 ml. of 1.6 molar n-butyllithium in hexane. The addition rate is adjusted so that the reaction temperature remains below −55° C. Ten minutes after the addition is complete, 48.2 g. of the reaction product of part B of this example and 50 ml. of tetrahydrofuran are added dropwise at such rate as to maintain the reaction temperature below −60° C.

The resulting mixture is then stirred at −75° C. for 2 hr. and then ambient temperature overnight. Acetic acid (20 ml.) is thereafter added and the resulting mixture distilled under vacuum, thereby removing most of the tetrahydrofuran. The residue is then shaken with diethyl ether in methylene chloride (3:1 by volume) and a cold dilute sodium bicarbonate solution. The organic layer is then washed with brine, dried, and concentrated. The residue was crystallized from diethyl ether, yielding 54 g. of dimethyl 3,3-dimethyl-2-oxo-4-phenylbutylphosphonate, the title compound. The melting point is 48°–50° C.

Following the procedure of Example 1, but using in place of benzyl chloride substituted benzyl chlorides of the formula

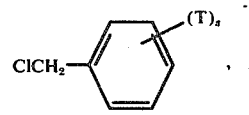

wherein T is fluoro, chloro, trifluoromethyl, alkyl of one to 3 carbon atoms, inclusive, or alkoxy of one to 3 carbon atoms, inclusive, and wherein s is zero, one, 2, or 3, with the proviso that not more than two T's are other than alkyl, and with the further proviso that the various T's may be the same or different, there are prepared the corresponding dimethyl-3,3-dimethyl-2-oxo-4-(substituted phenyl)butylphosphonates. For example, there is prepared by this procedure dimethyl 3,3-dimethyl-2-oxo-4-(p-fluorophenyl)butylphosphonate.

Further, following the procedure of Example 1, but using in place of the isobutyric acid of Example 1, part A, propionic acid, there is prepared dimethyl 3-methyl-2-oxo-4-phenylbutylphosphonate. Following the procedure of Example 1, but using the substituted benzyl chlorides described above in place of benzyl chloride and propionic acid in place of isobutyric acid there are prepared the various dimethyl 3-methyl-2-oxo-4-(substituted phenyl)-butylphosphonates wherein the phenyl substitution is as described above.

Further, following the procedure of Example 1, but using acetic acid in place of isobutyric acid as used in Example 1, part A, there is prepared dimethyl-2-oxo-4-phenylbutylphosphonate. Using acetic acid in combination with the various substituted benzyl chlorides described above according to the procedure of Example 1, there are prepared the various dimethyl 2-oxo-4-(substituted phenyl)-butyl phosphonates, wherein the phenol substitution is as described above.

Following the procedure of Example 1, but using 2,2-difluoroacetic acid in place of isobutyric acid as used in part A of Example 1, there is prepared dimethyl 3,3-difluoro-2-oxo-4-phenylbutylphosphonate. Further, following the procedure of Example 1, but using 2,2-difluoroacetic acid in combination with substituted benzyl chlorides described above, there are prepared the corresponding dimethyl 3,3-difluoro-2-oxo-4-substituted phenylbutylphosphonate, wherein the phenyl substitution is as described above.

Further, following the procedure of Example 1, but using 2-fluoroacetic acid in place of isobutyric acid there is prepared dimethyl 3-fluoro-2-oxo-4-phenylbutylphosphonate.

Using 2-fluoroacetic acid and the various substituted benzyl chlorides described above according to the procedure of Example 1, there are prepared the various dimethyl 3-fluoro-2-oxo-4-(substituted phenyl)butyl phosphonates, wherein the phenyl substitution is as described above.

EXAMPLE 2

1-t-butyldimethylsilyloxy-4-pentyne

4-Pentyne-1-ol (42 g.) and 100 ml. of dimethylformamide are flushed with nitrogen and combined with a solution of 90 g. of t-butyldimethylchlorosilane and 81.6 g. of imidazole in 150 ml. of dimethylformamide. The reaction temperature is maintained at 0°–5° C. The reaction mixture is then allowed to warm to 25° C. and stirred for 24 hr. Thereafter the resulting solution is cooled to 0°–5° C. and 10 ml. of water is added. After stirring for an additional 30 min. the crude product is extracted with hexane and the hexane layer is washed with water, sodium bisulfate, sodium bicarbonate, and brine; dried over anhydrous magnesium sulfate; filtered; and concentrated under reduced pressure to yield 87.7 g. of pure product. NMR absorptions are observed at 0.0, 0.84, 1.3-1.9, 1.68, 2.18, and 3.66 δ.

Following the procedure of Example 2, but using in place of 4-pentyne-1-ol, 5-hexyne-1-ol or 6-heptyne-1-ol, there are prepared the corresponding 1-t-butyldimethylsilyloxy-($\omega$-1)-alkynes.

EXAMPLE 3

(6-Carboxyhexyl)triphenylphosphoniumbromide.

A mixture of 63.6 g. of 7-bromoheptanoic acid, 80 g. of triphenylphosphine, and 30 ml. of acetonitrile, is refluxed for 68 hr. Thereafter 20 ml. of acetonitrile is removed by distillation. After the remaining solution is cooled to room temperature, 30 ml. of benzene is added with stirring. The mixture is then allowed to stand for 12 hr. A solid separates which is collected by filtration, yielding 134.1 g. of product, melting point 185°–187° C.

Following the procedure of Example 3, but using 3-bromopropionic acid, 4-bromobutanoic acid, 5-bromopentanoic acid, or 6-bromohexanoic acid, in place of 7-bromoheptanoic acid, there are prepared the corresponding ($\omega$-carboxyalkyl)triphenylphosphonium bromides.

EXAMPLE 4

3$\alpha$-Benzoyloxy-5$\alpha$-hydroxy-2$\beta$-(3-oxo-4,4-difluoro-trans-1-octenyl)-1$\alpha$-cyclopentaneacetic acid, $\gamma$ lactone (Formula XXII: $R_7$ is n-butyl, $R_{16}$ is benzoyloxy, $R_3$ and $R_4$ of the $L_1$ moiety are fluoro, and Y is trans—CH=CH—).

Refer to Chart A.

A. A solution of 24.3 g. of thallous ethoxide in 125 ml. of dry benzene is cooled in an ice bath, and thereafter a solution of 25.3 g. of dimethyl 3,3-difluoro-2-oxoheptylphosphonate in 75 ml. of benzene is added and thereafter rinsed with 50 ml. of benzene. The solution is stirred for 30 min. at 5° C. and thereafter 22.1 g. of crystalline 3$\alpha$-benzoyloxy-5$\alpha$-hydroxy-2$\beta$-carboxaldehyde-1$\alpha$-cyclopentaneacetic acid, $\gamma$ lactone is added rapidly. This reaction mixture is then stirred for 13 hr. at ambient temperature yielding a brown solution of pH 9–10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding 33.6 g. of an oil, which is then chromatographed on 600 g. of silica gel packed in 20 percent ethyl acetate in cyclohexane. Elution, collecting 500 ml. fractions, with 2 l. of 20 percent, 2 l. of 25 percent, and 4 l. of 30 percent ethyl acetate in cyclohexane yields 20.3 g. of crude product, which upon recrystallization from 240 ml. of diethyl ether in pentane (2:1) yields 13.3 g. of 3$\alpha$-benzoyloxy-5$\alpha$-hydroxy-2$\beta$-(3-oxo-4,4-difluoro-trans-1-octenyl)-1$\alpha$-cyclopentaneacetic acid, $\gamma$ lactone.

Alternatively this product is prepared by adding 3$\alpha$-benzoyloxy-2$\beta$-carboxaldehyde-5$\alpha$-hydroxy-1$\alpha$-cyclopentaneacetic acid $\gamma$ lactone (3 g.) in 30 ml. of dichloromethane to a solution of dimethyl 2-oxo-3,3-difluoroheptylphosphonate (6.69 g.) and sodium hydride (1.35 g.) in 15 ml. of tetrahydrofuran. The resulting reaction mixture is then stirred for 2 hr. at about 25° C., acidified with acetic acid, and concentrated under reduced pressure. The residue is partitioned between dichloromethane and water, and the organic phase is concentrated. The residue is chromatographed on silica gel, eluting with ethyl acetate in Skellysolve B (1:1).

Following the procedure of Example 4, but using in place of 3$\alpha$-benzoyloxy-5$\alpha$-hydroxy-2$\beta$-carboxaldehyde-1$\alpha$-cyclopentaneacetic acid $\gamma$ lactone, 5$\alpha$-hydroxy-2$\beta$-carboxaldehyde-1$\alpha$-cyclopentaneacetic acid $\gamma$ lactone, there is obtained 5$\alpha$-hydroxy-2$\beta$-(3-oxo-4,4-difluoro-trans-1-octenyl)-1$\alpha$-cyclopentaneacetic acid $\gamma$ lactone.

Further, following the procedure of Example 4, but using in place of dimethyl 2-oxo-3,3-difluoroheptylphosphonate, any of the various dimethyl phosphonates described hereinabove there are prepared the corresponding 3$\alpha$-benzoyloxy-5$\alpha$-hydroxy-1$\alpha$-cyclopentaneacetic acid $\gamma$ lactones or 5$\alpha$-hydroxy-1$\alpha$-cyclopentaneacetic acid $\gamma$ lactones with a 2$\beta$-(3-oxo-trans-1-alkenyl)-substituent, optionally substituted, as follows:

4,4-difluorohexenyl; 4,4-difluoroheptenyl; 4,4-difluorononenyl; 4,4-difluorodecenyl; 4-fluorohexenyl; 4-fluoroheptenyl, 4-fluorooctenyl; 4-fluorononenyl; 4-fluorodecenyl; 4,4-dimethylhexenyl; 4,4-dimethylheptenyl, 4,4-dimethyloctenyl; 4,4-dimethylnonenyl; 4,4-dimethyldecenyl; 4-methylhexenyl; 4-methylheptenyl, 4-methyloctenyl, 4-methylnonenyl; 4-methyldecenyl; hexenyl; heptenyl; octenyl; nonenyl; decenyl; 5-phenylpentyl; 5-(m-trifluoromethylphenyl)-pentenyl; 5-(m-fluorophenyl)-pentenyl; 5-(m-chlorophenyl)-pentenyl; 5-(p-trifluoromethylphenyl)-pentenyl; 5-(p-fluorophenyl)-pentenyl; 5-(p-chlorophenyl)-pentenyl; 4-methyl-5-phenylpentenyl; 4-methyl-5-(m-trifluoromethylphenyl)pentenyl; 4-methyl-5-(m-fluorophenyl)-pentenyl; 4-methyl-5-(p-trifluoromethylphenyl)-pentenyl; 4-methyl-5-(p-fluorophenyl)-pentenyl; 4-methyl-5-(p-chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-(m-chlorophenyl)-pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m- fluorophenyl)-pentenyl; 4-fluoro-5-(m-chlorophenyl)-pentenyl; 4-fluoro-5-(p-trifluoromethylphenyl)-pentenyl; 4-fluoro-5-(p-fluorophenyl)-pentenyl; 4-fluoro-5-(p-chlorophenyl)-pentenyl; 4,4-difluoro-5-phenylpentenyl; 4,4-difluoro-5-(m-trifluoromethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyl; 4-(p-chlorophenoxy)-butenyl; 4-methyl-4-phenoxybutenyl; 4-methyl-4-(m-trifluoromethylphenoxy)-butenyl; 4-methyl-4-(m-fluorophenoxy)-butenyl; 4-methyl-4-(m-chlorophenoxy)-butenyl; 4-methyl-4-(p-trifluoromethylphenoxy)-butenyl; 4-methyl-4-(p-fluorophenoxy)-butenyl; 4-methyl-4-(p-chlorophenoxy)-butenyl; 4,4-dimethyl-4-phenoxybutenyl; 4,4-dimethyl-4-(trifluoromethylphenoxy)-butenyl; 4,4-dimethyl-4-(m-fluorophenoxy)-butenyl; 4,4-dimethyl-4-(m-chlorophenoxy)-butenyl; 4,4-dimethyl-4-(p-trifluoromethylphenoxy)-butenyl; 4,4-dimethyl-4-(p-fluorophenoxy)-butenyl; 4,4-dimethyl-4-(p-chlorophenoxy)-butenyl; and the like.

EXAMPLE 5

$3\alpha$-Benzoyloxy-$5\alpha$-hydroxy-$2\beta$-[(3S)-3-hydroxy-trans-1-octenyl]-$1\alpha$-cyclopentaneacetic acid $\gamma$ lactone (Formula XXIV; $R_3$ and $R_4$ of the $L_1$ moiety are hydrogen, $R_5$ and $R_6$ of the $M_5$ moiety are hydrogen, $R_7$ is n-butyl, $R_{16}$ is benzoyloxy, and Y is trans—CH=CH—) or its (3R)- hydroxy epimer.

Sodium borohydride (2.86 g.) is slowly added to a stirred suspension of 12.6 g. of anhydrous zinc chloride in 78 ml. of dimethyl ether in ethylene glycol (glyme) with ice bath cooling. The mixture is stirred for 20 hr. at ambient temperature and thereafter cooled to −20° C. A solution of 8.0 g. of $3\alpha$-benzyloxy-$5\alpha$-hydroxy-$2\beta$-(3-oxo-cis-1-octenyl)-$1\alpha$-cyclopentaneacetic acid $\gamma$ lactone (prepared according to Example 4) in 80 ml. of glyme is added over a period of 15 min. Stirring is continued for 24 hour at −20° C. and thereafter 60 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield an oil, which when chromatographed on 900 g. of silica gel packed in one percent acetone and methylene chloride, eluting with one to 15 percent acetone in methylene chloride yields the epimerically pure title product.

Following the procedure of Example 5, but using in place of the $3\alpha$-benzoyloxy-$5\alpha$-hydroxy-$2\beta$-(3-oxo-trans-1-octenyl)-$1\alpha$-cyclopentaneacetic acid $\gamma$ lactone starting material employed therein, the various $3\alpha$-benzoyloxy-$5\alpha$-hydroxy-$2\beta$-(3-oxo-trans-1-alkenyl or substituted alkenyl)-$1\alpha$-cyclopentaneacetic acid $\gamma$ lactones there are prepared the corresponding (3R)- or (3S) hydroxy products.

Following the procedure of Example 5, but using in place of the $3\alpha$-benzoyloxy-$5\alpha$-hydroxy-$2\beta$-(3-oxo-trans-1-octenyl)-$1\alpha$-cyclopentaneacetic acid $\gamma$ lactone used therein, $5\alpha$-hydroxy-$2\beta$-(3-oxo-trans-1-alkenyl or substituted alkenyl)-$1\alpha$-cyclopentaneacetic acid $\gamma$ lactones described following Example 4, there are prepared the corresponding 3R or 3S-hydroxy products.

For example, there are obtained the above $3\alpha$-benzoyloxy-$5\alpha$-hydroxy- or $5\alpha$-hydroxy-$1\alpha$-cyclopentaneacetic acid $\gamma$ lactones wherein the $2\beta$-side chain in either the 3R or 3S form consists of 3-hydroxy-trans-1-hexenyl; 3-hydroxy-trans-1-heptenyl; 3-hydroxy-trans-1-non-enyl; 3-hydroxy-trans-1-decenyl; 3-hydroxy-4-methyl-trans-1-octenyl; 3-hydroxy-4,4-dimethyl-trans-1-octenyl; 3-hydroxy-4-fluoro-trans-1-octenyl; 3-hydroxy-4,4-difluoro-trans-1-octenyl; 3-hydroxy-5-phenyl-trans-1-pentenyl; 3-hydroxy-5-(p-fluorophenyl)-trans-1-pentenyl; 3-hydroxy-5-(m-chlorophenyl)-trans-1-pentenyl; 3-hydroxy-5-(m-trifluoromethylphenyl)-trans-1-pentenyl; 3-hydroxy-4,4-dimethyl-5-phenyl-trans-1-pentenyl; 3-hydroxy-4,4-dimethyl-5-(p-fluorophenyl)-trans-1-pentenyl; 3-hydroxy-4,4-dimethyl-5-(m-chlorophenyl)-trans-1-pentenyl; 3-hydroxy-4,4-dimethyl-5-(m-trifluoromethylphenyl)-trans-1-pentenyl; 3-hydroxy-4,4-difluoro-5-phenyl-trans-1-pentenyl; 3-hydroxy-4,4-difluoro-5-(p-fluorophenyl)-trans-1-pentenyl; 3-hydroxy-4,4-difluoro-5-(m-chlorophenyl)-trans-1-pentenyl; 3-hydroxy-4,4-difluoro-5-(m-trifluoromethylphenyl)-trans-1-pentenyl; 3-hydroxy-4-phenoxy-trans-1-butenyl; 3-hydroxy-4-(p-fluorophenoxy)-trans-1-butenyl; 3-hydroxy-4-(m-chlorophenoxy)-trans-1-butenyl; 3-hydroxy-4-(m-trifluoromethylphenoxy)-trans-1-butenyl; 3-hydroxy-4,4-dimethyl-4-phenoxy-trans-1-butenyl; 3-hydroxy-4,4-dimethyl-4-(p-fluorophenoxy)-trans-1-butenyl; 3-hydroxy-4,4-dimethyl-4-(m-chlorophenoxy)-trans-1-butenyl; 3-hydroxy-4,4-dimethyl-4-(m-trifluoromethylphenoxy)-trans-1-butenyl; and the like.

EXAMPLE 6

$3\alpha$-Benzoyloxy-$5\alpha$-hydroxy-$2\beta$-[(3RS)-$3\beta$hydroxy-3-methyl-trans-1-octenyl]-$1\alpha$-cyclopentaneacetic acid $\gamma$ lactone.

Refer to Chart A.

A solution of 18 g. of $3\alpha$-benzoyloxy-$5\alpha$-hydroxy-$2\beta$-(3-oxo-trans-1-octenyl)-$1\alpha$-cyclopentaneacetic acid $\gamma$ lactone in 890 ml. of dry benzene is cooled to 9° C. under a nitrogen atmosphere. A toluene solution of trimethylaluminum (60 ml.) is added over a period of 4 min. to the resulting mixture. This mixture is then stirred for 1.5 hr. at 20°–25° C. then cooled to 10° C. Thereupon 370 ml. of saturated ammonium chloride is slowly added at such a rate so as to maintain the reaction mixture at ambient temperature. After 0.5 hr. the reaction mixture is diluted with ethyl acetate and water and filtered, the filter cake being washed with the ethyl acetate-water solvent. The aqueous layer is extracted with ethyl acetate and the combined organic extracts are washed with brine, dried over magnesium sulfate, and evaporated to yield an oil, which is chromatographed on one kg. of silica gel packed in 10 percent ethyl acetate and Skellysolve B. Elution with 10 to 16 percent ethyl acetate in Skellysolve B (18 l.), 28 percent ethyl acetate in Skellysolve B (8 l.) yields title compound. Fractions as shown by thin layer chromatography to contain pure product are combined. Rechromatography, in the fashion described above, yields (3S)- or (3R)-epimer.

Omitting the chromatographic separation described above, the 3RS-epimeric mixture obtained on trimethylaluminum alkylation are separated in high yield as prostaglandin-type products.

Following the procedure of Example 6, but using in place of the 3-oxo lactone starting material therein, the various lactones described following Example 4, there are obtained 3-hydroxy-3-methyl products corresponding to each of the 3-hydroxy products of Example 5.

EXAMPLE 7

5α-Hydroxy-2β-[(3S)-3-hydroxy-trans-1-octenyl]-1α-cyclopentaneacetaldehyde, γ lactol, bis-(tetrahydropyranyl ether) (Formula XXVII: $R_3$ and $R_4$ of the $L_1$ moiety are hydrogen, $M_6$ is

$R_7$ is n-butyl, $R_{18}$ is tetrahydropyran-2-yloxy, and Y is trans—CH=CH—) or its (3R)epimer.

Refer to Chart A.

A. A solution of 5 g. of the reaction product of Example 5 in 150 ml. of methanol is purged with nitrogen. Thereafter, potassium carbonate (2.02 g.) is added and the resulting mixture is stirred at ambient temperature until thin layer chromatographic analysis shows the solvolysis to be complete (about 1.5 hr.). The methanol is then evaporated under reduced pressure. The residue is then shaken with ethyl acetate (250 ml.), brine (250 ml.), and 8 g. of potassium bisulfate. The aqueous layer is then extracted twice with 125 ml. of ethyl acetate and the organic extracts are dried over magnesium sulfate, and evaporated to yield an oil. This oil is then dissolved in chloroform and a few crystals of p-toluenesulfonic acid are added. When thin layer chromatography indicates the action is complete (about 2 hr.), the reaction mixture is then washed with aqueous potassium bicarbonate, dried, and evaporated to yield an oil which is then chromatographed using silica gel packed in one percent ethanol in methylene chloride for purification. Accordingly, the formula XXV deacylated lactone is prepared.

B. A solution of 1.57 g. of the reaction product of part A above, in 35 ml. of methylene chloride (containing 2.5 ml. of dihydropyran and 100 mg. of pyridine hydrochloride) is allowed to stand for 23 hr. at ambient temperature. The reaction mixture is then washed with water, aqueous potassium bicarbonate, dried over magnesium sulfate, and evaporated, yielding an oil which is thereafter chromatographed on 200 g. of silica gel packed in one percent acetone in methylene chloride. Elution with from one to ten percent acetone in methylene chloride yields the formula XXVI bis-tetrahydropyranyl lactone corresponding to the lactone reaction product of part A above.

C. A solution of the reaction product of part B above in 20 ml. of toluene is cooled to −70° C. and thereafter 10 ml. of 10 percent diisobutylaluminum hydride in toluene is slowly added. The reaction mixture is then stirred at −70° C. until thin layer chromatographic analysis indicates that the reduction is complete (about 30 min.). Thereafter the cooling bath is removed and 9 ml. of a mixture of tetrahydrofuran and water (2:1) is added slowly. The reaction mixture is then stirred and allowed to warm to room temperature, and is then filtered through Celite. The filter cake is rinsed with benzene, combined organic extracts are then dried over magnesium sulfate and evaporated to yield the title compound.

Following the procedure of Example 7, but using as starting material 3α-benzoyloxy-5α-hydroxy-2β-[(3R) or (3S)-3-hydroxy-3-methyl-trans-1-octenyl]-1α-cyclopentaneacetic acid γ lactone, there is obtained the corresponding bis-tetrahydropyranyl ether.

Following the procedure of Example 7, the 3α-benzoyloxy-5-hydroxy or 5-hydroxy lactones described in and following Example 5 or 6 are transformed into corresponding lactols.

Following the procedure of Example 5, but using the title compound of Example 4 as starting material, there is prepared 3α-benzoyloxy-5α-hydroxy-2β-[(3S)-4,4-difluoro-3-hydroxy-cis-1-octenyl]-1α-cyclopentaneacetaldehyde γ-lactol acid γ lactone or its (3R) epimer.

Following the procedure of Example 7, there is prepared 3α,5α-dihydroxy-2β-[(3S)-3-hydroxy-4,4-difluoro-trans-1-octenyl]-1α-cyclopentaneacetaldehyde γ lactol, bis-tetrahydropyranyl ether from the corresponding acylated lactone.

EXAMPLE 8

3α,5α-Dihydroxy-2β-[(3S)-3-hydroxy trans-1-octenyl]-1α-cyclopentanepropionaldehyde δ-lactol bis tetrahydropyranyl ether) (Formula XXXII: $n$ is 2, $R_3$ and $R_4$ of the $L_1$ moiety are hydrogen, $M_6$ is

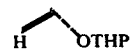

$R_7$ is n-butyl, $R_{18}$ is tetrahydropyranyloxy, and Y is trans—CH=CH—).

Refer to Chart A.

A. A suspension of methoxymethyltriphenylphosphonium chloride (32.4 g.) in 150 ml. of tetrahydrofuran is cooled to −15° C. To the suspension is added 69.4 ml. of n-butyllithium in hexane (1.6 molar) in 45 ml. of tetrahydrofuran. After 30 min. there is added a solution of 3α,5α-dihydroxy-2β-[(3S)-3-hydroxy-trans-1-octenyl]-1α-cyclopentaneacetaldehyde γ lactol bis-(tetrahydropyranyl)ether, Example 7 (10 g.), in 90 ml. of tetrahydrofuran. The mixture is stirred for 1.5 hr. while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXVIII product are combined.

B. The reaction product of part A above in 20 ml. of tetrahydrofuran is hydrolyzed with 50 ml. of 66 percent aqueous acetic acid at about 57° C. for 2.5 hr. The resulting mixture is then concentrated under reduced pressure. Toluene is added to the residue and the solution is again concentrated. Finally the residue is subjected to chromatography on silica gel, eluting with chloroform and methanol (6:1). The title compound is thereby obtained by combining and concentrating fractions as shown by thin layer chromatography to contain pure product. Accordingly, there is obtained the corresponding formula XXIX δ-lactol.

C. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part B above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol), (9:1), pure product is removed by filtration. The filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula XXX lactone.

D. The formula XXX lactone prepared in part C above is then transformed to its bis-tetrahydropyranyl ether derivative following the procedure described in Example 7, part B.

E. The formula XXXI compound prepared in part D above is then reduced to the corresponding title δ lactol bis-tetrahydropyranyl ether by the procedure described in Example 7, part C.

Following the procedure of Example 8, but using the corresponding (3R) starting material in place of the (3S) starting material there is obtained the corresponding (3R)-lactol product.

Following the procedure of Example 8, but using in place of the formula XXVII lactol, the various formula XXVII lactols described following Example 7, there are obtained the corresponding formula XXXII lactols wherein $n$ is 2.

EXAMPLE 9 cis-4,5-Didehydro-PGF$_{1\alpha}$, 11,15-bis-(tetrahydropyranyl) ether (Formula XXXIII: g is one, R$_3$ and R$_4$ of the L$_1$ moiety are hydrogen, M$_6$ is

Z$_5$ is cis—CH$_2$—CH=CH—, R$_1$ is hydrogen, R$_7$ is n-butyl, R$_{18}$ is tetrahydropyranyloxy, and Y is trans—CH=CH—) or its 15-epimer.

Refer to Chart A.

3-Carboxypropyltriphenylphosphonium bromide (prepared by heating 4-bromobutyric acid and triphenylphosphine in benzene at reflux for 18 hr., and thereafter purifying), 106 g., is added to sodiomethylsulfinylcarbanide prepared from sodium hydride (2.08 g., 57 percent) and 30 ml. of dimethylsulfoxide. The resulting Wittig reagent is combined with the formula XXXII lactol of Example 8 and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate and isomeric hexanes (3:1). Those fractions as shown to contain the desired compound by thin layer chromatography are combined to yield pure product.

Following the procedure of Example 9, but using in place of the (3S) starting material the corresponding (3R) starting material there is obtained the corresponding 15-epi-cis-4,5-didehydro-PGF$_{1\alpha}$ -type compound.

Following the procedure of Example 9, but using in place of the 3-carboxypropyltriphenylphosphonium bromide, 4-carboxybutyltriphenylphosphonium bromide, or 5-carboxypentyltriphenylphosphonium bromide, there are prepared the corresponding formula XXXIII compounds wherein g is 2 or 3.

Further, following the procedure of Example 9, but using in place of the formula XXXII starting material the various formula XXXII δ-lactols described following Example 8, there are prepared the corresponding cis-4,5-didehydro-PGF$_{1\alpha}$ -type bis-(tetrahydropyranyl ethers).

EXAMPLE 10

16-phenoxy-17,18,19,20-tetranor-PGF$_{2\alpha}$, methyl ester, 11,15-bis-tetrahydropyranyl ether (Formula XXXIII: g is one, R$_3$ and R$_4$ of the L$_1$ moiety are hydrogen, M$_6$ is

R$_1$ is methyl, Z$_5$ is cis—CH=CH—CH$_2$—, R$_7$ is phenoxy, R$_{18}$ is tetrahydropyranyloxy, and Y is trans—CH=CH—) or its 15-epimer.

Refer to Chart A.

A. Sodium hydride (0.57 g., 57 percent in mineral oil) in 25 ml. of dimethylsulfoxide, is added to 3 g. of 4-carboxybutyltriphenylphosphonium bromide. The reaction mixture is maintained at 20° C. with stirring for 30 min. A solution of 3α,5α-dihydroxy-2β-[(3R)-3-hydroxy-4-phenoxytrans-1-butenyl]-1α-cyclopentaneacetaldehyde γ-lactol bis(tetrahydropyranyl ether), 1.57 g., in 10 ml. of dimethylsulfoxide is added. The reaction mixture is stirred at ambient temperature for 2 hr. and diluted with 50 ml. of benzene. Potassium bisulfate (2.7 g. in 30 ml. of water) is slowly added, maintaining the reaction temperature at less than or equal to 10° C. The aqueous layer is extracted with 50 ml. of benzene and the organic extracts are washed successfully with 50 ml. of water and 50 ml. of brine before combining, drying, and evaporating. Evaporation yields an oil which is chromatographed on 100 g. of acid washed silica gel packed in 20 percent ethyl acetate and Skellysolve B. Elution with 20–75 percent ethyl acetate and Skellysolve B yields crude 16-phenoxy-17,18,19,20-tetranor-PGF$_{2\alpha}$, bis-(tetrahydropyranyl ether).

B. A solution of the crude reaction product of part A above and 15 ml. of diethyl ether is esterified with diazomethane, used in stoichiometric excess. The crude methyl ester is chromatographed on 100 g. of silica gel packed in 2 percent acetone methylene chloride. Elution with 2–12 percent acetone in methylene chloride yields the title compound.

Following the procedure of Example 10, but using the (3S)-lactol there is obtained the corresponding 15-epi-PGF$_{2\alpha}$ -type, methyl ester, 11,15-bis-tetrahydropyranyl ether.

Following the procedure of Example 10, but using 5-carboxypentyltriphenylphosphonium bromide or 6-carboxyhexyltriphenylphosphonium bromide in place of 4-carboxybutyltriphenylphosphonium bromide there is obtained the corresponding 2α-homo- or 2a,2b-dihomo-PGF$_{2\alpha}$ -type compound or its 15-epimer.

EXAMPLE 11

15-Methyl-17-phenyl-18,19,20-trinor-11-deoxy-PGF$_{2\alpha}$, methyl ester (Formula XXXIV: g is one, R$_3$ and R$_4$ of the L$_1$ moiety are hydrogen, M$_1$ is

R$_1$ is methyl, R$_7$ is benzyl, R$_8$ is hydrogen, Y is trans-CH=CH—, and Z$_5$ is cis-CH=CH—CH$_2$—) or its 15-epimer.

A. A solution of 5.7 g. of 5α-hydroxy-2β-[(3S)-3-hydroxy-3-methyl-5-phenyl-trans-1-pentenyl]-1α-cyclopentaneacetic acid γ lactone in 150 m. of tetrahydrofuran is cooled to −60° C. Diisobutylaluminum hydride and toluene (85 ml.) is added over a period of 23 min. at a temperature of −70° C. The reaction mixture is stirred for an additional 24 min. Thereafter 100 ml. of saturated aqueous ammonium chloride solution is slowly added at a temperature of −60° C. The resulting mixture is then stirred and allowed to warm to room temperature, yielding a gel as precipitate. This mixture is then diluted with 70 ml. of water and 150 ml. of ethyl acetate, mixed thoroughly and filtered. The filter cake is washed with water and ethyl acetate. The aqueous layer is extracted with ethyl acetate. The combined organic extracts are washed with brine, dried over sodium sulfate, and evaporated to yield a lactol corresponding to lactone starting material as a cloudy oil.

B. Following the procedure of Example 10, sodium hydride in dimethylsulfoxide is combined with 4-carboxybutyltriphenylphosphonium bromide and the reaction product of part A above to yield the title compound in free acid form.

The reaction product of part B above is esterified with diazomethane following the procedure described above, yielding the title compound.

The preparation of the above title compound or its 15-epimer is optionally accomplished following the procedure of Chart A wherein, the 3(RS)-3-methyl lactone as prepared following Example 6 is not subject to a chromatographic separation step. Thereby by the procedure of Example 7 prepares a corresponding 3(RS)-3-methyl lactol. Thereafter, following the procedure of Example 10, the (15RS)-15-methyl-17-phenyl-18,19,20-trinor-11-deoxy-PGF$_{2\alpha}$ -bis(tetrahydropyranyl ether), methyl ester is prepared by methyl esterification of the free acid so formed. The tetrahydropyranyl ether moieties may then be hydrolyzed and the C-15 epimer separated by chromatographic techniques.

Following the procedure of Example 11, or the optional procedure discussed above, there are prepared each 15-epi-15-methyl or 15-methyl-PGF$_{2\alpha}$ -type compound from the corresponding lactol described following Example 7.

EXAMPLE 12

15-Methyl-17-phenyl-18,19,20-trinor-11-deoxy-PGF$_{2\alpha}$ or its 15-epimer.

A solution of 2.0 g. of the reaction product of Example 11, or its 15-epimer, in 20 ml. of methanol is cooled to 0° C. The resulting mixture is thereafter treated dropwise under a nitrogen atmosphere with 12 ml. of 10 percent aqueous sodium hydroxide solution. The mixture is then allowed to warm to room temperature and stirred for 2 hr. After removal of the methanol by evaporation under reduced pressure the residue is diluted with water and extracted with methylene chloride. The aqueous layer is then cooled with ice, treated with 24 ml. of 2 molar aqueous sodium bisulfate solution and extracted immediately with ethyl acetate. The combined organic extracts are washed with brine, dried over anhydrous sodium sulfate, and concentrated. Crude product may then be chromatographed on 150 g. of silica gel, yielding the title compound or its 15-epimer.

Following the procedure of Example 12, but using any of the 15-methyl-PGF$_{2\alpha}$ - or 11-deoxy-15-methyl-PGF$_{2\alpha}$ -type, methyl esters, there are prepared corresponding free acid products.

EXAMPLE 13

16-phenoxy-17,18,19,20-tetranor-PGF$_{2\alpha}$ or its 15-epimer.

16-Phenoxy-17,18,19,20-tetranor-PGF$_{2\alpha}$ -bis(tetrahydropyranyl ether) (0.60 g.) is reacted with 30 ml. of tetrahydrofuran, water, and acetic acid (1:3:6) at 40° C. for 4 hr. Thereafter, the resulting mixture is diluted with 60 ml. of water and freeze dried. The residue is then extracted with diethyl ether and washed with aqueous potassium bicarbonate and brine. The diethyl ether extract is then dried using magnesium sulfate and evaporated to yield an oil which is chromatographed to yield pure product.

Using corresponding 15-epimeric starting material the corresponding 15-epimeric product is prepared.

EXAMPLE 14

4,4,5,5-Tetradehydro-PGF$_{1\alpha}$ (Formula LXXVIII: g is one; R$_1$, R$_3$, and R$_4$ of the L$_1$ moiety and R$_5$ and R$_6$ of the M$_1$ moiety are all hydrogen; R$_7$ is n-butyl; and R$_8$ is hydroxy) or its methyl ester.

Refer to Chart C.

A. 3α,5α-Dihydroxy-2β-[(3S)-3-hydroxy-trans-1-octenyl]-1α-cyclopentaneacetic acid γ-lactone (26.8 g.) and 30 ml. of dimethylformamide are combined with 40.8 g. of imidazole and 45 g. of t-butyldimethylsilylchloride in 70 ml. of dimethylformamide, the reactants being cooled to 0°–5° C. The mixture is then allowed to warm to room temperature and stirred for 4 hr. Thereafter, the reaction mixture is again cooled to 0°–5° C., ice water is added, and stirring is continued for an additional 10 min. Thereupon crude formula LXXII compound (R$_{38}$ is t-butyldimethylsilyloxy) is extracted with hexane; washed with 100 ml. of water, sodium bisulfate, sodium bicarbonate, and brine; dried over magnesium sulfate; and evaporated under reduced pressure. Crude product is then purified by crystallization yielding 43.9 g. NMR absorptions are observed at 0.06, 0.88, 0.7–1.1, 1.1–2.7, 3.66–4.2, 4.68–5.06, and 5.38–5.56 δ. Infrared absorptions are observed at 775, 875, 860, 915, 975, 1030, 1095, 1120, 1165, 1215, 1250, 1360, 1460, 1470, and 1750 cm.$^{-1}$. The mass spectrum shows base peak absorption at 481.3185 and other peaks at 439, 425, 365, 349, and 307.

B. The reaction product of Example 2, (20.3 g.) a  d 340 ml. of diethyl ether are combined and cooled to −20° to −30° C. under a nitrogen atmosphere. Thereafter 59 ml. of methyllithium is added to the ethereal mixture and stirred for 15 min. Then a solution of 26.6 g. of the reaction product of part A and 100 ml. of dry diethyl ether is prepared under a nitrogen atmosphere.

The previously prepared alkynyl lithium reagent is added to the starting material dropwise. The reaction mixture is stirred for 45 min. and thereafter quenched by addition of 100 ml. of aqueous ammonium chloride and additional powdered ammonium chloride. This resulting mixture is then stirred for 1.5 hr. and thereafter extracted with diethyl ether. The organic layers are washed with brine and ammonium chloride, dried over anhydrous magnesium sulfate, filtered, and concentrated under reduced pressure. Thereafter the crude product so obtained is purified by silica gel chromatography eluting with dichloromethane. Thereby, 35.2 g. of pure formula LXXIII product are obtained. NMR absorptions are observed at 0.00, 0.84, 0.68–1.08, 1.08–2.9, 3.66, 3.70–4.22, and 5.26–5.46 $\delta$.

C. The reaction product of part B (31.4 g.) and 15 ml. of dimethylformamide are combined under a nitrogen atmosphere at room temperature. Thereafter 9.2 g. of imidazole and 10.2 g. of t-butyldimethylchlorosilane in 30 ml. of dimethylformamide are added to the previously prepared solution. Stirring continues at room temperature for 21 hr. Thereupon the reaction mixture is cooled to 0°–5° C., water is added, and after 15 min. crude product is extracted with a mixture of diethyl ether and hexane (1:1). Thereafter, the extract is washed with sodium bicarbonate, sodium bisulfate, and brine; dried over magnesium sulfate; filtered; and concentrated. The crude product so obtained is then chromatographed on 1.5 kg. of silica gel eluting with dichloromethane and hexane (1:1). Thereupon 26.5 g. of pure formula LXXIV product is obtained. NMR absorptions are observed at 0.02, 0.04, 0.06, 0.68–1.08, 0.86–0.88, 1.08–3.1, 3.70, 3.94–4.36, and 5.34–5.56 $\delta$. Infrared absorptions are observed at 2210, 1680, 1225, 1105, 1070, 1005, 895, 835, and 775 cm.$^{-1}$. The mass spectrum shows base peak absorption at 751.5050.

D. Sodium borohydride (3.4 g.) and 517 ml. of methanol are combined with cooling to $-20°$ C. under a nitrogen atmosphere. Thereafter the reaction product of step C (24.2 g.) in 517 ml. of methanol is slowly added to the previously prepared sodium borohydride solution. The reaction mixture is then warmed to 0°–5° C. in an ice water bath. After 1.5 hr. the reaction is quenched by addition of aqueous ammonium chloride and thereafter allowed to warm to room temperature. The solvent is then removed by evaporation and the resulting crude product extracted with diethyl ether; washed with water and brine; and dried over anhydrous magnesium sulfate. Filtration and concentration under reduced pressure yield 23.3 g. of crude formula LXXV product. This product is then used without further purification. NMR absorptions are observed at 0.06, 0.88, 1.10–2.6, 3.66, 3.88–4.30, 4.30–4.62, and 5.32–5.64. Infrared absorptions are observed at 3500, 2950, 2900, 2220, 1480, 1390, 1360, 1260, 1100, 1010, 975, 940, 900, 840, and 775 cm.$^{-1}$.

E. The reaction product of part D (8.5 g.) in 10.5 ml. of pyridine is cooled to 0°–5° C. and thereafter 4.0 g. of p-toluenesulfonyl chloride is added. This mixture is then stirred until it becomes clear, and thereafter allowed to stand at 0°–5° C. for 24 hr. Thereupon additional p-toluenesulfonyl chloride is added. The reaction is thereafter complete in about 48–72 hr. While maintaining reaction temperature at 0°–5° C. 1 ml. of water is then added. Thereupon the mixture is allowed to warm to room temperature, and the product extracted with 2 l. of diethyl ether. The ethereal layer is then washed with water, sodium bisulfate, sodium bicarbonate, and brine; dried over magnesium sulfate; and filtered through Celite. Concentration under reduced pressure yields the tosylate of the formula LXXV compound. Thereupon, the tosylate produced above is immediately subjected to lithium aluminum hydride reduction. Accordingly, 3.99 g. of lithium aluminum hydride under a nitrogen atmosphere is dissolved in 220 ml. of diethyl ether, maintaining the reaction temperature at 0°–5° C. Therefter the tosylate (dissolved in 111 ml. of diethyl ether) is added dropwise. The resulting mixture is then allowed to warm to room temperature and stirred for about 24 hr. Thereupon, the reaction mixture is cooled to 0°–5° C. and saturated sodium sulfate is added until a gray precipitate forms. The mixture is then diluted with 1 l. of diethyl ether and dried over sodium sulfate. Filtration and concentration under reduced pressure yields crude product which is optionally purified using high pressure liquid chromatography eluting with a mixture of benzene, hexane, and acetone (10:10:1) to obtain 4.3 g. of the formula LXXVI compound. NMR absorptions are observed at 0.02, 0.88, 1.1–2.6, 3.62, 3.82–4.22, and 5.26–5.52. Infrared absorptions are observed at 2950, 2930, 2890, 2850, 1470, 1465, 1360, 1255, 1125, 1105, 1070, 1005, 970, 840, and 775 cm.$^{-1}$. The mass spectrum shows base peak absorption at 794.5960.

F. The reaction product of part E (3.3 g.) and 84 ml. of tetrahydrofuran, water, and trifluoroacetic acid (8:2:1) are combined. This mixture is then stirred at room temperature for 24 hr. and thereafter aqueous sodium bicarbonate is added, whereby the pH is adjusted to 7 or 8. This resulting mixture is then saturated with sodium chloride, and extracted with ethyl acetate. The organic layer is washed, dried, filtered, and concentrated to yield crude product. Purification is accomplished by high pressure liquid chromatography eluting with chloroform and acetone (1:1) thereby, 1.3 g. of pure formula LXXVII product are obtained. Characteristic NMR absorptions are observed at 3.08–5.12, and 5.12–6.06 $\delta$. Characteristic infrared absorptions are observed at 3500, 2950, 2900, 1440, 1340, 1060, 1010, 970, and 950 cm.$^{-1}$. The mass spectrum shows base peak absorption at 626.3999.

G. Platinum oxide (1.52 g.) and 112 ml. of water are alternately flushed with hydrogen over a period of 15 min. Thereafter the system is flushed with nitrogen and evacuated over a period of 10 min. Finally, oxygen is bubbled through the mixture for 10 min., sodium carbonate is added, and thereafter 1.3 g. of the reaction product of part F (dissolved in 50 ml. of water and acetone; 4:1). This resulting mixture is then placed in an oil bath at 58° C. and stirred for 3 hr. during which oxygen is bubbled through. Thereafter the resulting mixture is filtered and washed in an acetone bath. Thereafter the solvent is removed under reduced pressure. This crude product is then acidified with sodium bisulfate, whereby pH is adjusted to 3, and thereafter extracted with ethyl acetate. Thereafter the extract is washed with brine, dried over anhydrous sodium sulfate, filtered, and concentrated. Crystallization from ethyl acetate and cyclohexane yields 299 mg. of the pure formula LXXVIII title acid. Infrared absorptions are observed at 3420, 2950, 2700, 2630, 1715, 1435, 1410, 1320, 1215, 1090, 1065, 1055, 1020, 1000, 980, and 970 cm.$^{-1}$. The mass spectrum shows base peak absorption at 640.3838.

H. The free acid of part G is esterified with excess ethereal diazomethane and thereafter subjected to high pressure liquid chromatography, yielding the title methyl ester. NMR absorptions are observed at 0.68–1.1, 1.10–2.68, 2.46, 3.50, 3.68, 3.78–4.33, and 5.32–5.6 δ. Infrared absorptions are observed at 3420, 1735, 1670, 1320, 1290, 1195, 1175, 1090, 1065, 1055, 1020, 1005, 980, and 970 cm.$^{-1}$. The mass spectrum shows base peak absorption at 582.3587.

Following the procedure of Example 17, but using the formula LXXI lactone of the (3R)-3-hydroxy configuration there is obtained the corresponding 15-epi-4,4,5,5-tetradehydro-PGF$_{1\alpha}$ -type product.

Further, following the procedure of Example 14, but using various lactones described in and following Example 5 or in and following Example 6 (which are deacylated according to the procedure of Example 7, part A), there are prepared the corresponding 4,4,5,5-tetradehydro-PGF$_{1\alpha}$ - or 4,4,5,5-tetradehydro-11-deoxy-PGF$_{1\alpha}$ -type products.

Further, following the procedure of Example 14, but substituting in part B of Example 14 the 1-t-butyldimethylsilyloxy-(ω-1)-alkynyl compound described following Example 2 and optionally substituting the various lactones described in the preceeding paragraph in part A of Example 14, there are prepared the corresponding 2a-homo- or 2a,2b-dihomo- 4,4,5,5-tetradehydro-PGF$_{1\alpha}$ - or 11-deoxy-PGF$_{1\alpha}$ -type compounds described herein.

EXAMPLE 15

4,4,5,5-Tetradehydro-PGE$_1$, methyl ester (Formula LXXIX: R$_1$ is methyl, R$_3$ and R$_4$ of the L$_1$ moiety and R$_5$ and R$_6$ of the M$_1$ moiety are hydrogen, R$_7$ is n-butyl, R$_8$ is hydroxy, and g is 1. )

Refer to Chart C.

A. The methyl ester of Example 14 (439.2 mg.) in 1.2 ml. of dimethylformamide are cooled to 0°–5° C. and thereafter 450 mg. of t-butyldimethylchlorosilane and 408 mg. of imidazole in 1.2 ml. of dimethylformamide is added. This mixture is allowed to stand for 24 hr. at 0°–5° C. The mixture is then stirred with addition of 1 to 2 ml. of water. After 10 min. the resulting mixture is extracted with diethyl ether and hexane (1:1). The organic layer is washed with sodium bisulfate, and brine and dried over anhydrous magnesium sulfate. Concentration under reduced pressure yields 447 g. of crude product. Chromatography yields two products, the more polar, 412.8 mg., being the 11,15-bis-(t-butyldimethylsilyl ether) derivative of the starting material.

B. 618 mg. of pyridine and 10 ml. of methylene chloride are combined with 390 mg. of chromic acid which mixture is then stirred for 15 min. Thereafter the reaction product of part A (385 mg.) in 3.5 ml. of methylene chloride is added and stirring is continued for one hr. The layers are then separated and a tar-containing layer is washed well with diethyl ether, and these combined ethereal layers are then washed with sodium bisulfate, sodium bicarbonate, sodium bisulfite, and brine and dried over anhydrous sodium sulfate. Filtration and concentration under vacuum yield 384 mg. of crude PGE-type, 11,15-bis(t-butyldimethylsilyl ether).

C. The crude product from part B is hydrolyzed in 6.5 ml. of a mixture of tetrahydrofuran water and trifluoroacetic acid (8:2:1) at 25° C. After 7 hr. the reaction mixture is neutralized by addition of saturated sodium bicarbonate (adjusted pH to 7 or 8) and is stirred for 30 min. at 25° C. The reaction mixture is then extracted with chloroform and the chloroform extract is washed with sodium bicarbonate and brine and dried over anhydrous magnesium sulfate. Concentration under reduced pressure yields crude product (250 mg.) which is then purified using preparative thin layer chromatography (chloroform and aceonte, 2=1). Thereby, 126.5 mg. of pure title product is obtained. NMR absorptions are observed at 0.68–1.08, 1.13.1, 2.46, 3.2–4.0, 3.68, 3.88–4.55, and 5.54–5.75 δ. Infrared absorptions are observed at 3400, 2950, 2920, 2850, 1740, 1435, 1365, 1295, 1245, 1200, 1160, 1075, 1035, 1015, and 970 cm.$^{-1}$. The mass spectrum shows base peak absorption at 508.3020.

EXAMPLE 16

4,4,5,5-Tetradehydro-PGE$_{1\alpha}$

Refer to Chart C.

A. Following the procedure of Example 14, parts A, B, C, D, E, and F, but using as starting material 3α,5α-dihydroxy-2β-[(3S)-3-hydroxy-trans-1-octenyl]-1α-cyclopentaneacetic acid γ-lactone, bis-(tetrahydropyranyl ether) in place of the lactone starting material of part A of Example 14, there is prepared the 11,15-bis-(tetrahydropyranyl ether) of the reaction product of part F of Example 14. NMR absorptions are observed at 0.68–1.1, 1.1–2.52, 2.80, 3.62, 3.2–4.28, 4.58–4.78, and 5.24–5.68 δ. Characteristic infrared absorptions are observed at 3440, 2940, 2860, 1665, 1130, 1110, 1075, 1020, and 975 cm.$^{-1}$. The mass spectrum shows peaks at 650.4382.

B. The reaction product of part A. (2.28 g.) in 90 ml. of acetone is combined with 13 ml. of Jones reagent in 180 ml. of acetone by dropwise addition. The solution is maintained at −20° C. for a period of 10 min. The resulting mixture is then vigorously stirred at −15° C. for an additional 15 min. The reaction is then quenched by addition of 10 ml. of isopropanol. The acetone is then removed by evaporation and the residue combined with 200 ml. of brine and extracted with chloroform. The chloroform extracts are then washed with a sodium bisulfate and sodium chloride mixture and with brine. After drying over anhydrous sodium sulfate concentration under reduced pressure yields 2.3 g. of a crude 11,15-bis-(tetrahydropyranyl ether) of the title product.

C. The crude product of part B is then stirred in 45 ml. of a mixture of acetic acid, water, and tetrahydrofuran (50:25:2) at 45° C. for 6 hr. The mixture is then evaporated (azeotroping with toluene) and purified by high pressure liquid chromatography. Purification by high pressure liquid chromatography yields pure title product. Characteristic NMR absorptions are observed at 2.46, 3.84–4.34, 5.52–5.30, and 6.34 δ. The mass spectrum shows base peak absorption at 566.3294.

Following the procedure of either Example 15 or Example 16 there is prepared in either free acid or methyl ester form each of the 4,4,5,5-tetradehydro-PGE$_1$- or 11-deoxy-PGE$_1$-type compounds corresponding to each of the 4,4,5,5-tetradehydra-PGF$_{1\alpha}$ - or 11-deoxy-PGF$_{1\alpha}$ -type compounds described following Example 14.

EXAMPLE 17

5,6-Didehydro-15-methyl-17-phenyl-18,19,20-trinor-11-deoxy-PGF$_{2\alpha}$ , methyl ester (Formula XXXVII: R$_1$ is methyl, R$_3$ and R$_4$ of the L$_1$ moiety are both hydrogen, R$_5$ of the M$_1$ moiety is methyl, R$_7$ is benzyl, R$_8$ is hydrogen, and Z$_1$ is —C ≡ C—(CH$_2$)$_3$—).

Refer to Chart A.

A. The reaction product of Example 11 (4.56 g.) and 20 ml. of pyridine is subjected to dropwise addition of 4.0 g. of benzoyl chloride. The reaction mixture is then stirred at 25° C. for 16 to 24 hr. The reaction mixture is then cooled to 0° C., adding 5 ml. of water, stirring for 10 min., and thereafter extracting with diethyl ether. The ethereal layers are then washed with sodium bisulfate, sodium bicarbonate, and brine; dried over anhydrous magnesium sulfate; filtered; and concentrted under reduced pressure to yield crude formula XXXV product which is purified by high pressure liquid chromatography.

B. The reaction product of part A (5.9 g.) and 5 mg. of potassium carbonate are dissolved in 200 ml. of chloroform stirring under a nitrogen atmosphere at −20° C. Thereafter 1.6 g. of bromine in 10 ml. of chloroform is added over a period of 10 min. The reaction mixture is stirred for an additional 15 min. and concentrated under reduced pressure. The product thus obtained (the 5,6-dibromo- derivative of the starting material is then reacted in a solution containing 15.2 g. of 1,5-diazobicyclo-[5.4.0]-undec-5-ene (DBU) in 40 ml. of dioxane at 100° C. The reaction is maintained under a nitrogen atmosphere for 7 hr. and thereafter cooled to 25° C. for an additional 16 hr. The resulting mixture is then acidified with sodium bisulfate and extracted with 2 l. of diethyl ether. The ethereal layer is then washed with sodium bisulfate, sodium bicarbonate, and brine, and dried over anhydrous magnesium sulfate. Concentration under reduced pressure yields crude formula XXXVI product.

C. The crude product of part B is placed in a solution of 250 ml. of 2 percent potassium carbonate in methanol and stirred at 25° C. for 24 hr. The resulting mixture is then acidified to pH 4 or 5 with sodium bisulfate and concentrated to a residue which is extracted with ethyl acetate. The ethyl acetate extracts are then washed with brine and dried over anhydrous magnesium sulfate. The resulting mixture is then concentrated under vacuum with excess ethereal diazomethane added to esterify a partially hydrolyzed free acid. This product is then purified by high pressure liquid chromatography using ethyl acetate and chloroform (2:1) as solvent. Pure title product is thereby obtained.

EXAMPLE 18

5,6-Didehydro-15-methyl-17-phenyl-18,19,20-trinor-11-deoxy-PGE$_2$, methyl ester (Formula XL: $R_1$ is methyl, $R_3$ and $R_4$ of the $L_1$ moiety are both hydrogen, $R_5$ is methyl, $R_7$ is benzyl, $R_8$ is hydrogen, Y is trans—CH=CH—, and $Z_1$ is cis—CH=CH—(CH$_2$)$_3$—).

Refer to Chart A.

Following the procedure of Example 15, but using as starting material the compound of Example 17, the title compound of this example is prepared.

EXAMPLE 19

5,6-Didehydro-16-phenoxy-17,18,19,20-tetranor-PGF$_{2\alpha}$, methyl ester or 5,6-Didehydro-16-phenoxy-17,18,19,20-tetranor-PGE$_2$, methyl ester.

Refer to Chart A.

A. Following the procedure of Example 17, parts A-C, the reaction product of Example 10 is transformed to the formula XLIV compound: 5,6-didehydro-16-phenoxy-17,18,19,20-tetranor-PGF$_2$, methyl ester, 11,15-bis-(tetrahydropyranyl ether).

B. Following the procedure of Example 15, part B, the reaction product of part A is oxidized to form the bis ether of the formula XLV compound: 5,6-didehydro-16-phenoxy-17,18,19,20-tetranor-PGE$_2$, methyl ester, 11,15-bis-(tetrahydropyranyl ether).

C. Following the procedure of Example 13, the bis-(tetrahydropyranyl ether) of the reaction products of part A or part B is hydrolyzed to yield respectively the formula XLIII or XLV title compound.

EXAMPLE 20

5,6-Didehydro-PGD$_2$ or 5,6-didehydro-PGD$_2$, methyl ester (Formula LVI).

Refer to Chart B.

A. 5,6-Didehydro-PGF$_{2\alpha}$ (2.0 g.) and methylene chloride (50 ml.) is treated with 688 mg. of n-butyl boronic acid. The reaction mixture is then stirred vigorously and heated at reflux, adding 5 ml. aliquots of methylene chloride to replace amounts lost through evaporation. The procedure is continued for about 25 min. adding about 20 to 25 ml. of methylene chloride. The resulting distillate becomes clear. Thereafter 10 ml. of dihydropyran is added to the reaction mixture followed by addition of pyridine hydrochloride (150 mg.). After 20 hr. the reaction is complete and the methylene chloride is removed under reduced pressure and the residue combined with 30 ml. of methanol and 13 ml. of a 3N aqueous potassium hydroxide solution. The resulting solution is allowed to stand for 2 hr. and thereafter treated with 5 ml. of 30 percent hydrogen peroxide and 30 ml. of water. The methanol is then removed under reduced pressure and the aqueous residue diluted with 100 ml. of water and extracted twice with diethyl ether. The aqueous layer is then acidified with 25 ml. of 2N aqueous potassiumm bisulfate and extracted with ethyl acetate. The combined organic extracts are then combined, washed with brine, and dried over anhydrous sodium sulfate. Removal of solvent under reduced pressure yields 3.3 g. of an oil which is chromatographed on 100 g. of acid washed silica gel. The column is packed with and eluted with 75 percent ethyl acetate in hexane. The formula LIV 5,6-didehydro-PGF$_{2\alpha}$, 15-(tetrahydropyranyl ether) is thereby obtained.

B. 5,6-Didehydro-PGF$_{2\alpha}$, 15-(tetrahydropyranyl ether) (2 g.) in acetone (75 ml.) is cooled to −45° C. and thereafter treated with 1.2 ml. of the Jones reagent. The mixture is stirred for 30 min. at −35° C. to −45° C. and thereafter treated with 0.5 ml. of isopropanol and stirred an additional 15 min. The reaction mixture is then poured into a mixture of ice, water, and diethyl ether. The mixture is then extracted with diethyl ether and the combined ethereal extracts washed with brine, and dried over sodium sulfate. After filtration removal of solvent proceeds by rotary evaporation. Crude product (1.8 g.) thereby obtained is chromatographed on 360 g. of silica gel eluting with 45 percent ethyl acetate in hexane. 5,6-Didehydro-PGD$_2$, 15-tetrahydropyranyl ether (800 mg.) is thereby obtained.

C. 5,6-Didehydro-PGD$_2$, 15-(tetrahydropyranyl ether) (800 mg.) in 20 ml. of acetic acid and 10 ml. of water is heated at 40° C. for 2 hr. and then diluted with 100 ml. of water and thereafter freeze dried. The residue is then chromatographed on 50 g. of acid washed silica gel packed with 20 percent ethyl acetate in hexane. Elution with 35 to 65 percent ethyl acetate in hexane yields title product.

D. Esterification with excess ethereal diazomethane yields the title methyl ester.

Following the procedure of Example 20, but using any of the various 5,6-didehydro-PGF-type compounds described herein or known in the art there are prepared the corresponding 5,6-didehydro-PGD-type compounds.

Example 21

5,6-Didehydro-9-deoxy-9,10-didehydro-PGD$_2$ (Formula LVII: R$_1$ is hydrogen, Z$_1$ is cis-CH=CH-(CH$_2$)$_3$-, Y is trans-CH=CH-, R$_3$ and R$_4$ of the L$_1$ moiety and R$_5$ of the M$_1$ moiety are all hydrogen, and R$_7$ is n-butyl).

Refer to Chart B.

Quantities of 5,6-didehydro-PGD$_2$ are subject to silica gel chromatography until about 3.9 g. of less polar (than PGD$_2$) impurities are obtained from eluant fractions.

The 3.9 g. of less polar impurities are then chromatographed on 11.2 g. of silica gel packed with 5 percent acetone in methylene chloride eluting with 10 to 15 percent acetone in methylene chloride. Partially purified title product (1.2 g.), thereby obtained, is chromatographed on 200 g. of neutral silica gel packed with ethyl acetate, methanol, and chloroform (1:1:18). This column is washed with 800 ml. of ethyl acetate, methanol, and chloroform (1:1:48) and the above partially purified product thereafter added to the column. Eluting with ethyl acetate, methanol, and chloroform (1:1:48) pure title product.

EXAMPLE 22

9-Deoxy-5,6-didehydro-PGD$_2$ (Formula LXI: R$_1$ is hydrogen, R$_3$ and R$_4$ of the L$_1$ moiety and R$_5$ of the M$_1$ moiety are all hydrogen, R$_7$ is n-butyl, and Z$_1$ is cis-CH=CH-(CH$_2$)$_3$—).

Refer to Chart B.

A. Following the procedure of Example 21, the reaction product of Example 20, part C, is dehydrated to yield 5,6-didehydro-9,10-didehydro-9-deoxy-PGD$_2$, 15-tetrahydropyranyl ether.

B. To a stirred solution of the reaction product of step A dissolved in methanol at −20° C. under a nitrogen atmosphere there is added a solution of sodium borohydride in water and methanol. The resulting mixture is stirred for 20 min. and thereafter acetic acid is added cautiously. The resulting mixing is then concentrated and water is added and the pH is adjusted to about 3 with the addition of citric acid. The mixture is extracted with dichloromethane and the combined organic extracts are washed with water and brine and dried and concentrated to yield a formula LIX compound.

C. To a solution of the reaction product of step B dissolved in acetone at −20° C., there is added dropwise with stirring over one min. the Jones reagent (chromium trioxide, water, and concentrated sulfuric acid). The resulting mixture is then stirred at −20° C. for 20 min. and thereafter isopropanol is added and the mixture is stirred at −20° C. for an additional 10 min. The mixture is then diluted with water and extracted with diethyl ether. The ethereal extracts are then washed with water and brine, dried, and concentrated. The residue is then chromatographed on silica gel yielding pure formula LX product.

D. The title compound is then prepared by hydrolysis of the C-15 blocking group by the procedure of Example 13.

Following the procedures of the above examples, there are prepared each of the compounds named in Tables A-D below. Additionally, each corresponding methyl ester or a pharmacologically acceptable salt of each of the free acids named in these Tables is prepared as described hereinabove.

In the interpretation of these Tables each formula depicts a PG-type compound whose full name is provided combining the name provided below the formula with each of the designations provided in the "Name" column of the Table.

Table A

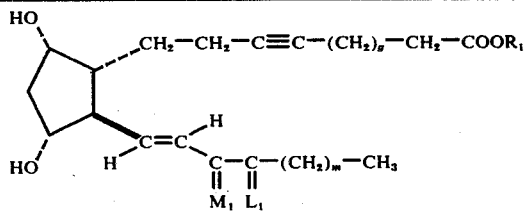

4,4,5,5-Tetradehydro-PGF$_{1\alpha}$-type compounds

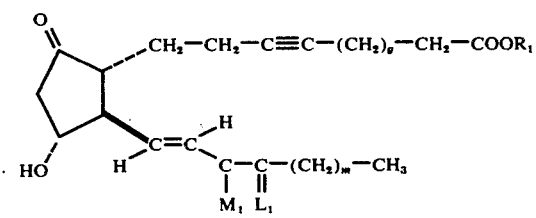

4,4,5,5-Tetradehydro-PGE$_1$-type compounds

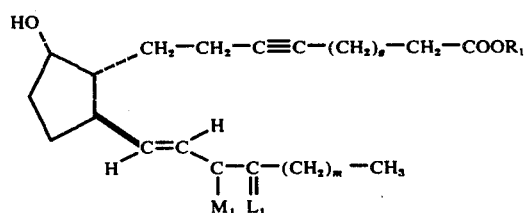

4,4,5,5-Tetradehydro-11-deoxy-PFG$_{1\alpha}$-type compounds

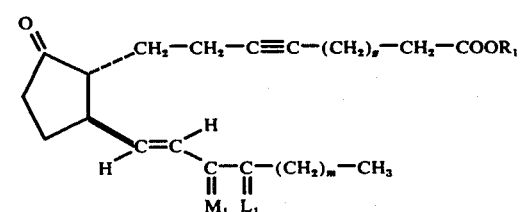

4,4,5,5-Tetradehydro-11-deoxy-PGE$_1$-type compounds

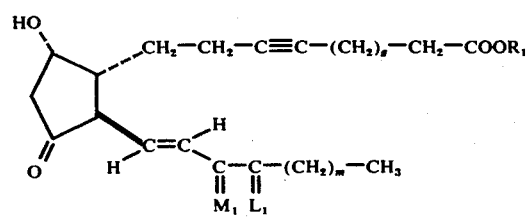

4,4,5,5-Tetradehydro-PGD$_1$-type compounds

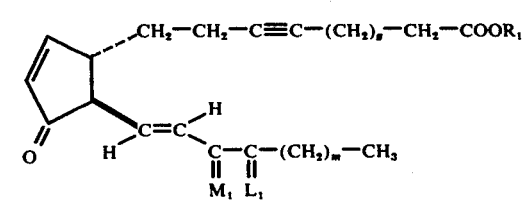

-continued 4,4,5,5-Tetradehydro-9-deoxy-9,10-didehydro-PGD$_1$-type compounds

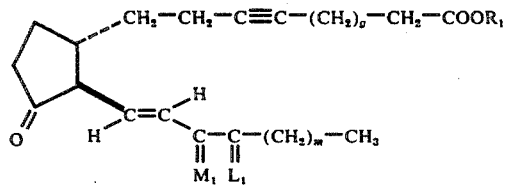

4,4,5,5-Tetradehydro-9-deoxy-PGD$_1$-type compounds

-continued

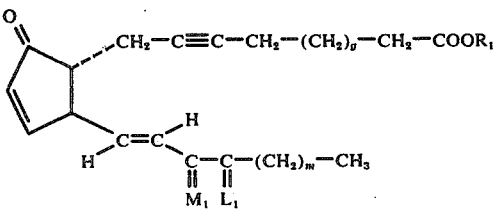

5,6-Didehydro-PGA$_2$ compounds

Table A

| Example | g | m | $L_1$ $R_3$ | $R_4$ | $M_1$ $R_5$ | ~OH | $R_1$ | Name |
|---|---|---|---|---|---|---|---|---|
| A-1 | 1 | 3 | methyl | hydrogen | hydrogen | α | hydrogen | 16-methyl |
| A-2 | 1 | 3 | methyl | hydrogen | methyl | α | hydrogen | 15,16-dimethyl |
| A-3 | 1 | 3 | methyl | hydrogen | hydrogen | α | hydrogen | (title compound) |
| A-4 | 1 | 3 | methyl | methyl | hydrogen | α | hydrogen | 16,16-dimethyl |
| A-5 | 1 | 3 | methyl | methyl | methyl | α | hydrogen | 15,16,16-trimethyl |
| A-5 | 1 | 3 | fluoro | hydrogen | hydrogen | α | hydrogen | 16-fluoro |
| A-6 | 1 | 3 | fluoro | hydrogen | methyl | α | hydrogen | 15-methyl-16-fluoro |
| A-7 | 1 | 3 | fluoro | fluoro | hydrogen | α | hydrogen | 16,16-difluoro |
| A-8 | 1 | 3 | fluoro | fluoro | methyl | α | hydrogen | 15-methyl-16,16-difluoro |
| A-9 | 1 | 3 | hydrogen | hydrogen | hydrogen | α | hydrogen | (title compound) |
| A-10 | 3 | 3 | hydrogen | hydrogen | hydrogen | α | hydrogen | 2a,2b-dihomo |
| A-11 | 3 | 3 | methyl | methyl | hydrogen | α | hydrogen | 2a,2b-dihomo-16,16-dimethyl |
| A-12 | 3 | 3 | methyl | methyl | methyl | α | hydrogen | 2a,2b-dihomo-15,16,16-trimethyl |
| A-13 | 3 | 3 | fluoro | fluoro | hydrogen | α | hydrogen | 2a,2b-dihomo-16,16-difluoro |
| A-14 | 3 | 3 | fluoro | fluoro | methyl | α | hydrogen | 2a,2b-dihomo-15-methyl-16,16-difluoro |

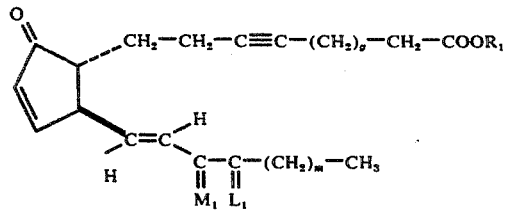

4,4,5,5-Tetradehydro-PGA$_1$-type compound

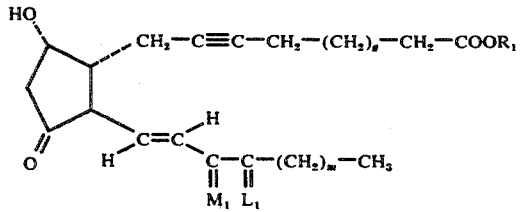

5,6-Didehydro-PGD$_2$-type compounds.

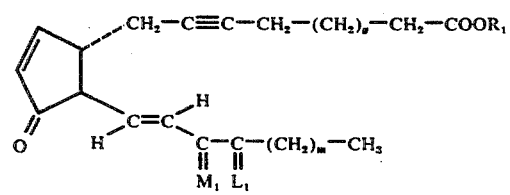

5,6-Didehydro-9-deoxy-9,10-didehydro-PGD$_2$-type compounds

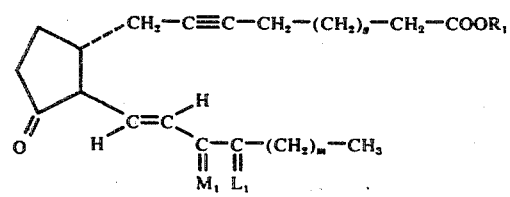

5,6-Didehydro-9-deoxy-PGD$_2$-type compounds

Table B

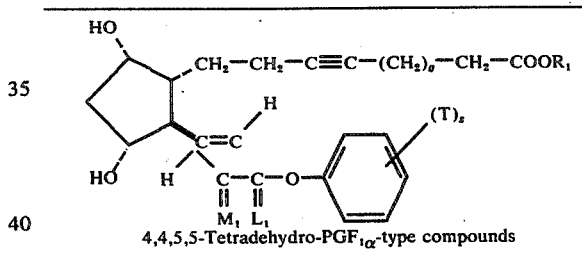

4,4,5,5-Tetradehydro-PGF$_{1\alpha}$-type compounds

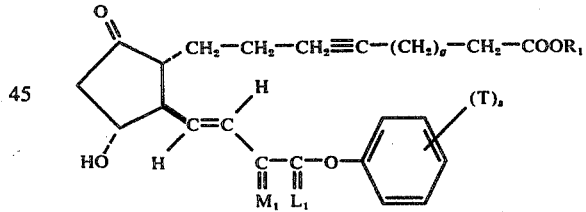

4,4,5,5-Tetradehydro-PGE$_1$-type compounds

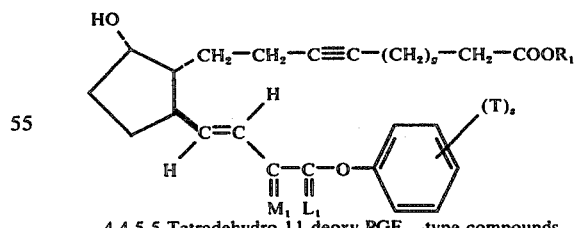

4,4,5,5-Tetradehydro-11-deoxy-PGF$_{1\alpha}$-type compounds

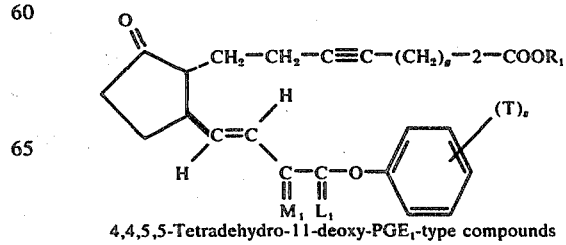

4,4,5,5-Tetradehydro-11-deoxy-PGE$_1$-type compounds

Table B-continued

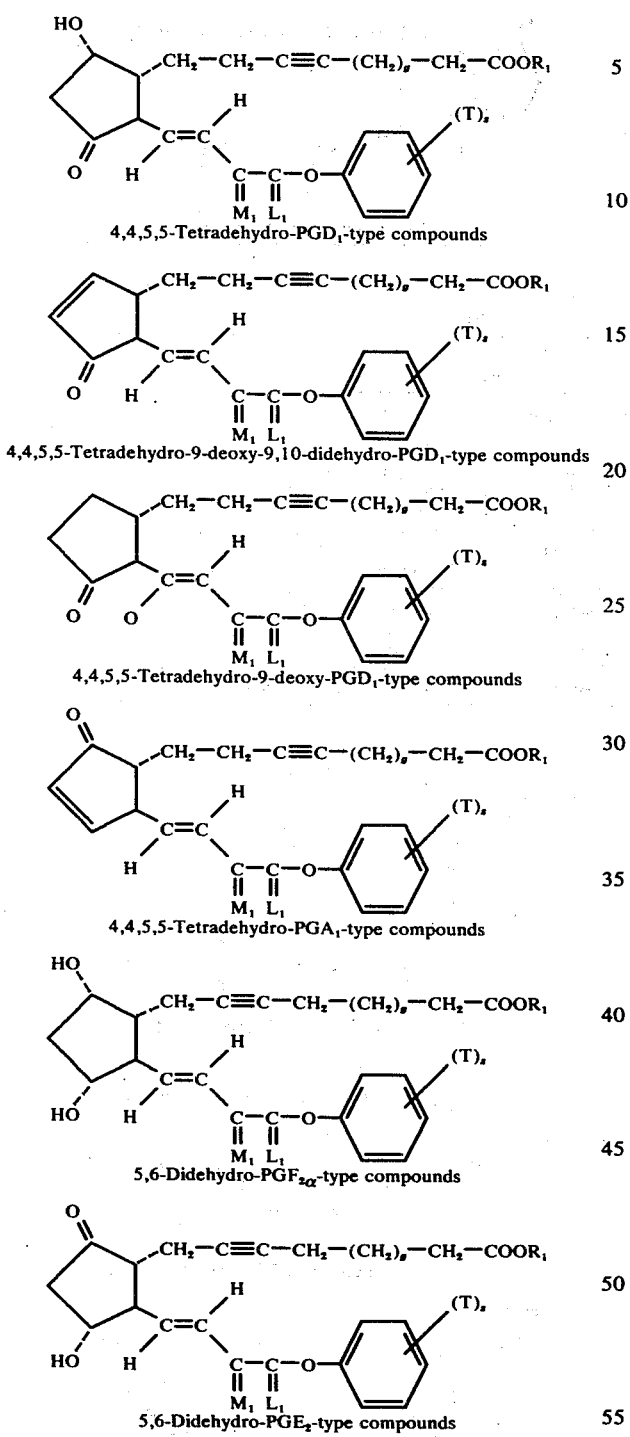

Table B-continued

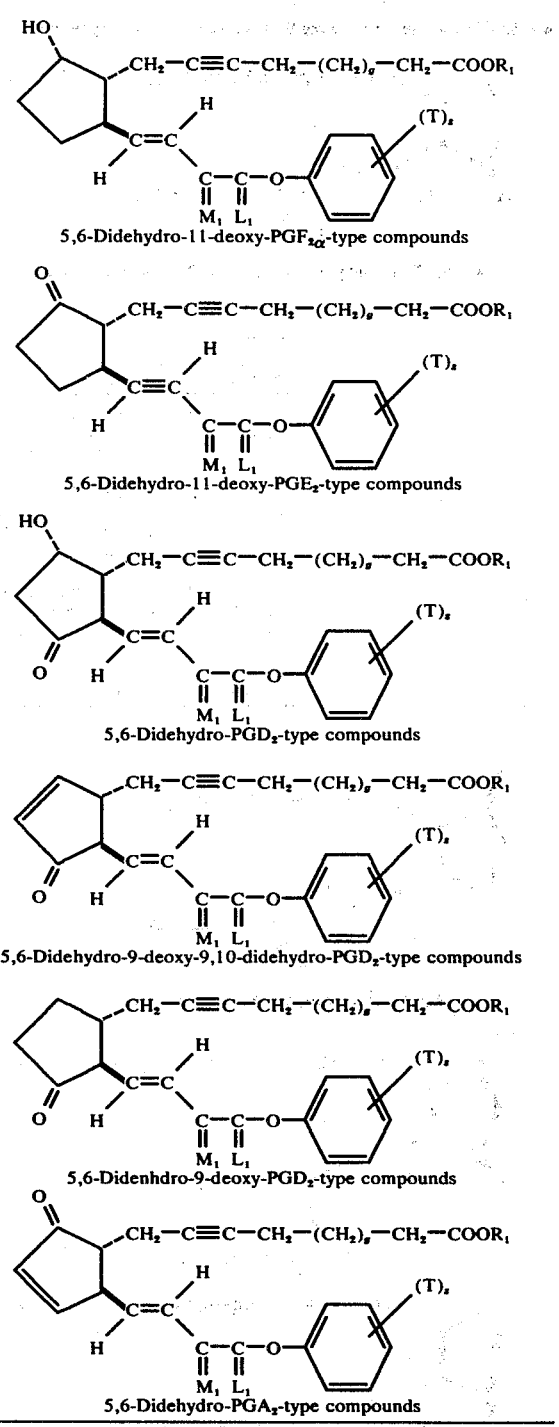

Table B

| Example | g | s | T | L₁ R₃ | R₄ | M₁ R₅ | ~OH | R₁ | Name |
|---|---|---|---|---|---|---|---|---|---|
| B-1 | 1 | 0 | | hydrogen | hydrogen | hydrogen | α | hydrogen | 16-phenoxy-17,18,19,20-tetranor |
| B-2 | 1 | 1 | p-fluoro | hydrogen | hydrogen | hydrogen | α | hydrogen | 16-(p-fluorophenoxy)-17,18,19,20-tetranor |
| B-3 | 1 | 1 | m-chloro | hydrogen | hydrogen | hydrogen | α | hydrogen | 16-(m-chlorophenoxy)-17,18,19,20-tetranor |
| B-4 | 1 | 1 | m-trifluoromethyl | hydrogen | hydrogen | hydrogen | α | hydrogen | 16-(m-trifluoromethylphenoxy)-17,18,19,20-tetranor |
| B-5 | 1 | 0 | | hydrogen | hydrogen | methyl | α | hydrogen | 15-methyl-16-phenoxy-17,18,19,20-tetranor |

Table B-continued

| Example | g | s | T | L₁ R₃ | R₄ | M₁ R₅ | ~OH | R₁ | Name |
|---|---|---|---|---|---|---|---|---|---|
| B-6 | 1 | 1 | p-fluoro | hydrogen | hydrogen | methyl | α | hydrogen | 15-methyl-16-(p-fluorophenoxy)-17,18,19,20-tetranor |
| B-7 | 1 | 1 | m-chloro | hydrogen | hydrogen | methyl | α | hydrogen | 15-methyl-16-(m-chlorophenoxy) |
| B-8 | 1 | 1 | m-trifluoromethyl | hydrogen | hydrogen | methyl | α | hydrogen | 15-methyl-16-(m-trifluoromethylphenoxy) |
| B-9 | 1 | 0 | | methyl | methyl | hydrogen | α | hydrogen | 16-methyl-16-phenoxy-18,19,20-trinor |
| B-10 | 1 | 1 | p-fluoro | methyl | methyl | hydrogen | α | hydrogen | 16-methyl-16-(p-fluorophenoxy)-18,19,20-trinor |
| B-11 | 1 | 1 | m-chloro | methyl | methyl | hydrogen | α | hydrogen | 16-methyl-16-(m-chlorophenoxy)-18,19,20-trinor |
| B-12 | 1 | 1 | m-trifluoromethyl | methyl | methyl | hydrogen | α | hydrogen | 16-methyl-16-(m-trifluoromethylphenoxy)-18,19,20-trinor |
| B-13 | 1 | 0 | | methyl | methyl | methyl | α | hydrogen | 15,16-dimethyl-16-phenoxy-18,19,20-trinor |
| B-14 | 1 | 1 | p-fluoro | methyl | methyl | methyl | α | hydrogen | 15,16-dimethyl-16-(p-fluorophenoxy)-18,19,20-trinor |
| B-15 | 1 | 1 | m-chloro | methyl | methyl | methyl | α | hydrogen | 15,16-dimethyl-16-(m-chlorophenoxy)-18,19,20-trinor |
| B-16 | 1 | 1 | m-trifluoromethyl | methyl | methyl | methyl | α | hydrogen | 15,16-dimethyl-16-(m-trifluoromethylphenoxy)-18,19,20-trinor |
| B-17 | 3 | 0 | | hydrogen | hydrogen | hydrogen | α | hydrogen | 2a,2b-dihomo-16-phenoxy-17,18,19,20-tetranor |
| B-18 | 3 | 1 | p-fluoro | hydrogen | hydrogen | hydrogen | α | hydrogen | 2a,2b-dihomo-16-(p-fluorophenoxy)-17,18,19,20-tetranor |
| B-19 | 3 | 1 | m-chloro | hydrogen | hydrogen | hydrogen | α | hydrogen | 2a,2b-dihomo-16-(m-chlorophenoxy)-17,18,19,20-tetranor |
| B-20 | 3 | 1 | m-trifluoromethyl | hydrogen | hydrogen | hydrogen | α | hydrogen | 2a,2b-dihomo-16-(m-trimethylphenoxy)-17,18,19,20-tetranor |
| B-21 | 3 | 0 | | hydrogen | hydrogen | methyl | α | hydrogen | 2a,2b-dihomo-15-methyl-16-oxy-17,18,19,20-tetranor |
| B-22 | 3 | 1 | p-fluoro | hydrogen | hydrogen | methyl | α | hydrogen | 2a,2b-dihomo-15-methyl-16-(p-fluorophenoxy)-17,18,19,20-tetranor |
| B-23 | 3 | 0 | m-chloro | hydrogen | hydrogen | methyl | α | hydrogen | 2a,2b-dihomo-15-methyl-16-(m-chlorophenoxy)-17,18,19,20-tetranor |
| B-24 | 3 | 1 | m-trifluoromethyl | hydrogen | hydrogen | methyl | α | hydrogen | 2a,2b-dihomo-15-methyl-16-(m-trifluoromethylphenoxy)-17,18,19,20-tetranor |

Table C

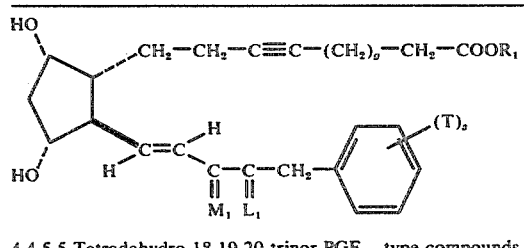

4,4,5,5-Tetradehydro-18,19,20-trinor-PGF$_{1α}$-type compounds

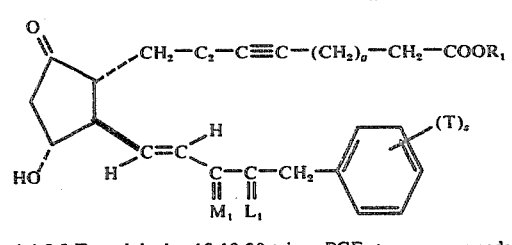

4,4,5,5-Tetradehydro-18,19,20-trinor-PGE$_1$-type compounds

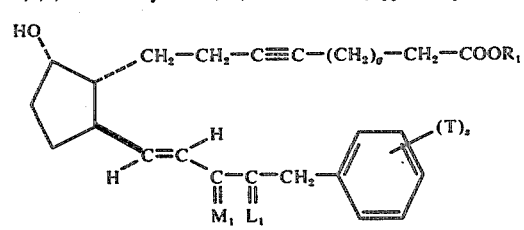

4,4,5,5-Tetradehydro-18,19,20-trinor-11-deoxy-PGF$_{1α1}$α-type compounds

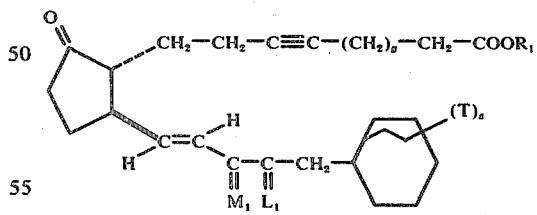

4,4,5,5-Tetradehydro-18,19,20-trinor-11-deoxy-PGE$_1$-type compounds

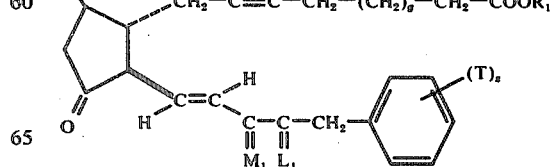

5,6-Didehydro-18,19,20-trinor-PGD$_2$-type compounds

Table C-continued

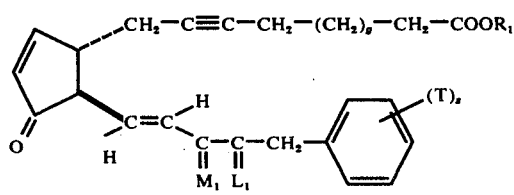

5,6-Didehydro-18,19,20-trinor-9-deoxy-9,10-.
-type compounds

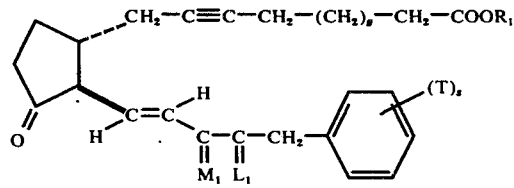

5,6-Didehydro-18,19,20-trinor-9-deoxy-PGD$_2$-type compounds

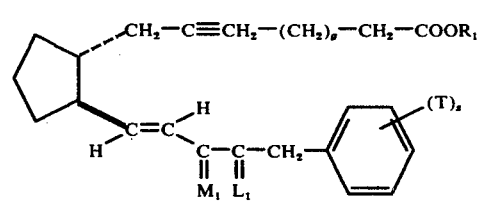

5,6-Didedhydro-18,19,20-trinor-11-deoxy-PGF$_{2\alpha}$-type compounds

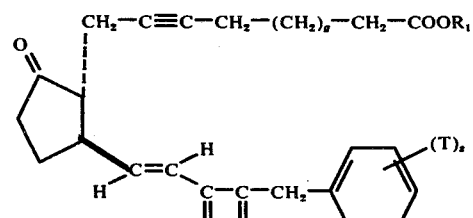

5,6-Didehydro-18,19,20-trinor-11-deoxy-PGE$_2$-type compounds

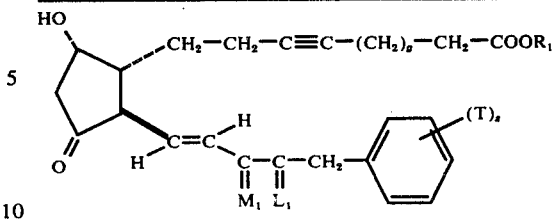

4,4,5,5-Tetradehydro-18,19,20-trinor-PGD$_1$-type compounds

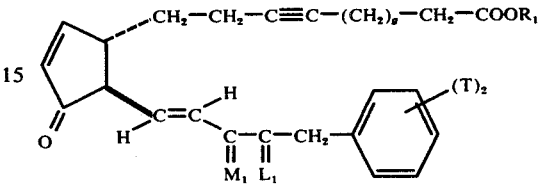

4,4,5,5-Tetradehydro-18,19,20-trinor-9-dexoy-9,10-didehydro-PGD$_1$-type compounds

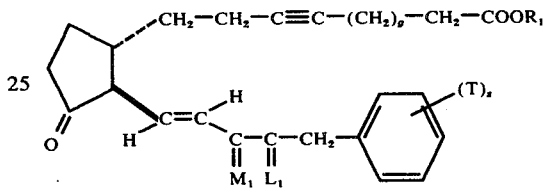

9βD-Tetradehydro-18,19,20-trinor-9-deoxy PGD1-type compounds

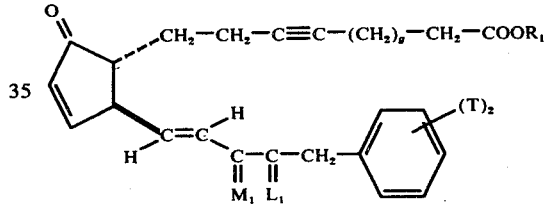

4,4,5,5-Tetradehydro-18,19,20-trinor-PGA$_1$-type compounds

Table C

| Example | g | s | T | L$_1$ R$_3$ | R$_4$ | M$_1$ R$_5$ | ~OH | R$_1$ | Name |
|---|---|---|---|---|---|---|---|---|---|
| C-1 | 1 | 0 | | hydrogen | hydrogen | hydrogen | α | hydrogen | 17-phenyl |
| C-2 | 1 | 1 | p-fluoro | hydrogen | hydrogen | hydrogen | α | hydrogen | 17-(p-fluorophenyl) |
| C-3 | 1 | 1 | m-chloro | hydrogen | hydrogen | hydrogen | α | hydrogen | 17-(m-chlorophenyl) |
| C-4 | 1 | 1 | m-trifluoromethyl | hydrogen | hydrogen | hydrogen | α | hydrogen | 17-(m-trifluoromethylphenyl) |
| C-5 | 1 | 0 | | hydrogen | hydrogen | methyl | α | hydrogen | 15-methyl-17-phenyl |
| C-6 | 1 | 1 | p-fluoro | hydrogen | hydrogen | methyl | α | hydrogen | 15-methyl-17-(p-fluorophenyl) |
| C-7 | 1 | 1 | m-chloro | hydrogen | hydrogen | methyl | α | hydrogen | 15-methyl-17-m(chlorophenyl) |
| C-8 | 1 | 1 | m-trifluoromethyl | hydrogen | hydrogen | methyl | α | hydrogen | 15-methyl-17-(m-trifluoromethylphenyl) |
| C-9 | 1 | 0 | | methyl | methyl | hydrogen | α | hydrogen | 16,16-dimethyl-17-phenyl |
| C-10 | 1 | 1 | p-fluoro | methyl | methyl | hydrogen | α | hydrogen | 16,16-dimethyl-17-(p-fluorophenyl) |
| C-11 | 1 | 1 | m-chloro | methyl | methyl | hydrogen | α | hydrogen | 16,16-dimethyl-17-(m-chlorophenyl) |
| C-12 | 1 | 1 | m-trifluoromethyl | methyl | methyl | hydrogen | α | hydrogen | 16,16-dimethyl-17-(m-trifluoromethylphenyl) |
| C-13 | 1 | 0 | | methyl | methyl | methyl | α | hydrogen | 15,16,16-trimethyl-17-phenyl |
| C-14 | 1 | 1 | p-fluoro | methyl | methyl | methyl | α | hydrogen | 15,16,16-trimethyl-17-(p-fluorophenyl) |
| C-15 | 1 | 1 | m-chloro | methyl | methyl | methyl | α | hydrogen | 15,16,16-trimethyl-17-(m-chlorophenyl) |
| C-16 | 1 | 1 | m-trifluoromethyl | methyl | methyl | methyl | α | hydrogen | 15,16,16-trimethyl-(m-trifluoromethylphenyl) |
| C-17 | 3 | 0 | | hydrogen | hydrogen | hydrogen | α | hydrogen | 2a,2b-dihomo-17-phenyl |
| C-18 | 3 | 1 | p-fluoro | hydrogen | hydrogen | hydrogen | α | hydrogen | 2a,2b-dihomo-17-(p-fluorophenyl) |
| C-19 | 3 | 1 | m-chloro | hydrogen | hydrogen | hydrogen | α | hydrogen | 2a,2b-dihomo-17-(m-chloro- |

Table C-continued

| Example | g | s | T | L₁ R₃ | R₄ | M₁ R₅ | ~OH | R₁ | Name |
|---|---|---|---|---|---|---|---|---|---|
| C-20 | 3 | 1 | m-trifluoro | hydrogen | hydrogen | hydrogen | α | hydrogen | 2a,2b-dihomo-17-(m-trifluorophenyl) |
| C-21 | 3 | 0 |  | hydrogen | hydrogen | methyl | α | hydrogen | 2a,2b-dihomo-15-methyl-17-phenyl |
| C-22 | 3 | 1 | p-fluoro | hydrogen | hydrogen | methyl | α | hydrogen | 2a,2b-dihomo-15-methyl-17-(p-fluorophenyl) |
| C-23 | 3 | 0 | m-chloro | hydrogen | hydrogen | methyl | α | hydrogen | 2a,2b-dihomo-15-methyl-17-(m-chlorophenyl) |
| C-24 | 3 | 1 | m-trifluoromethyl | hydrogen | hydrogen | methyl | α | hydrogen | 2a,2b-dihomo-15-methyl-17-(m-trifluoromethylphenyl) |
| C-25 | 1 | 0 |  | fluoro | fluoro | hydrogen | α | hydrogen | 16,16-difluoro-17-phenyl |
| C-26 | 1 | 1 | p-fluoro | fluoro | fluoro | hydrogen | α | hydrogen | 16,16-difluoro-17-(p-fluorophenyl) |
| C-27 | 1 | 1 | m-chloro | fluoro | fluoro | hydrogen | α | hydrogen | 16,16-difluoro-17-(m-chlorophenyl) |
| C-28 | 1 | 1 | m-trifluoromethyl | fluoro | fluoro | hydrogen | α | hydrogen | 16,16-difluoro-17-(m-trifluoromethylphenyl) |
| C-29 | 1 | 0 |  | fluoro | fluoro | methyl | α | hydrogen | 15-methyl-16,16-difluoro-17-phenyl |
| C-30 | 1 | 1 | p-fluoro | fluoro | fluoro | methyl | α | hydrogen | 15-methyl-16,16-difluoro-17-(p-fluorophenyl) |
| C-31 | 1 | 1 | m-chloro | fluoro | fluoro | methyl | α | hydrogen | 15-methyl-16,16-difluoro-17-(m-chlorophenyl) |
| C-32 | 1 | 1 | m-trifluoromethyl | fluoro | fluoro | methyl | α | hydrogen | 15-methyl-16,16-difluoro-17-(m-trifluoromethyl)phenyl) |

Table D

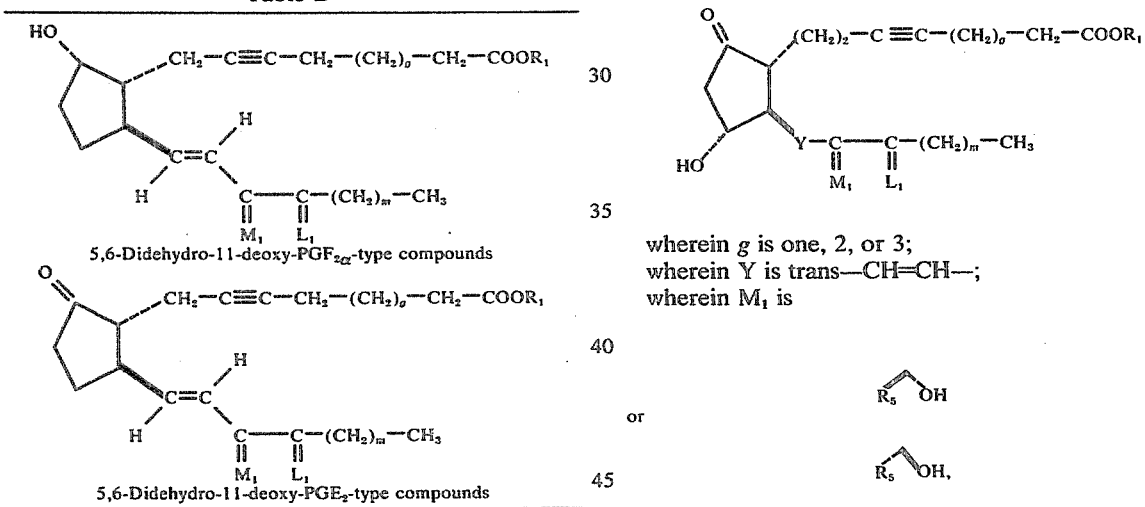

5,6-Didehydro-11-deoxy-PGF$_{2\alpha}$-type compounds 5,6-Didehydro-11-deoxy-PGE$_2$-type compounds wherein $g$ is one, 2, or 3;
wherein Y is trans—CH=CH—;
wherein M₁ is

or wherein R₅ is hydrogen or methyl; wherein $m$ is one to

Table D

| Example | g | m | L₁ R₃ | R₄ | M₁ R₅ | ~OH | R₁ | Name |
|---|---|---|---|---|---|---|---|---|
| D-1 | 1 | 3 | methyl | hydrogen | hydrogen | α | hydrogen | 16-methyl |
| D-2 | 1 | 3 | methyl | hydrogen | methyl | α | hydrogen | 15,16-dimethyl |
| D-3 | 1 | 3 | methyl | methyl | hydrogen | α | hydrogen | 16,16-dimethyl |
| D-4 | 1 | 3 | methyl | methyl | methyl | α | hydrogen | 15,16,16-trimethyl |
| D-5 | 1 | 3 | fluoro | hydrogen | hydrogen | α | hydrogen | 16-fluoro |
| D-6 | 1 | 3 | fluoro | hydrogen | methyl | α | hydrogen | 15-methyl-16-fluoro |
| D-7 | 1 | 3 | fluoro | fluoro | hydrogen | α | hydrogen | 16,16-difluoro |
| D-8 | 1 | 3 | fluoro | fluoro | methyl | α | hydrogen | 15-methyl-16,16-difluoro |
| D-9 | 3 | 3 | hydrogen | hydrogen | hydrogen | α | hydrogen | 2a,2b-dihomo |
| D-10 | 3 | 3 | methyl | methyl | hydrogen | α | hydrogen | 2a,2b-dihomo-16,16-dimethyl |
| D-11 | 3 | 3 | methyl | methyl | methyl | α | hydrogen | 2a,2b-dihomo-15,16,16-trimethyl |
| D-12 | 3 | 3 | fluoro | fluoro | hydrogen | α | hydrogen | 2a,2b-dihomo-16,16-difluoro |
| D-13 | 3 | 3 | fluoro | fluoro | methyl | α | hydrogen | 2a,2b-dihomo-15-methyl-16,16-difluoro |

5, inclusive; wherein L₁ is

I claim:
1. A prostaglandin analog of the formula

-continued or a mixture of

and

wherein $R_3$ and $R_4$ are hydrogen, methyl, or fluoro, being the same or different, with the proviso that one of $R_3$ and $R_4$ is fluoro only when the other is hydrogen or fluoro; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive phenyl, phenyl substituted with one, two, or three chloro or alkyl of one to 3 carbon atoms, inclusive, or a pharmacologically acceptable cation.

2. A compound according to claim 1, wherein $M_1$ is

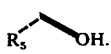

3. A compound according to claim 1, wherein $M_1$ is

4. A compound according to claim 3, wherein $g$ is 3.
5. A compound according to claim 4, wherein $m$ is 3.
6. A compound according to claim 5, wherein $R_3$, $R_4$, and $R_5$ are all hydrogen.
7. 2a,2b-Dihomo-4,4,5,5-tetradehydro-PGE$_1$, methyl ester, a compound according to claim 6.
8. A compound according to claim 3, wherein $g$ is one.
9. A compound according to claim 8, wherein $m$ is 3.
10. A compound according to claim 9, wherein $R_3$ and $R_4$ are both hydrogen.
11. A compound according to claim 10, wherein $R_5$ is methyl.
12. 4,4,5,5-Tetradehydro-15-methyl-PGE$_1$, methyl ester, a compound according to claim 11.
13. 4,4,5,5-Tetradehydro-15-methyl-PGE$_1$, a compound according to claim 11.
14. A compound according to claim 10, wherein $R_5$ is hydrogen.
15. 4,4,5,5-Tetradehydro-PGE$_1$, a compound according to claim 14.
16. 4,4,5,5-Tetradehydro-PGE$_1$, methyl ester, a compound according to claim 14.
17. A compound according to claim 9, wherein at least one of $R_3$ and $R_4$ is methyl.
18. A compound according to claim 17, wherein $R_3$ and $R_4$ are both methyl.
19. A compound according to claim 18, wherein $R_5$ is methyl.
20. 4,4,5,5-Tetradehydro-15,16,16-trimethyl-PGE$_1$, a compound according to claim 19.
21. 4,4,5,5-Tetradehydro-15,16,16-trimethyl-PGE$_1$, methyl ester, a compound according to claim 19.
22. A compound according to claim 18, wherein $R_5$ is hydrogen.
23. 4,4,5,5-Tetradehydro-16,16-dimethyl-PGE$_1$, a compound according to claim 22.
24. 4,4,5,5-Tetradehydro-16,16-dimethyl-PGE$_1$, methyl ester, a compound according to claim 22.
25. A compound according to claim 9, wherein at least one of $R_3$ and $R_4$ is fluoro.
26. A compound according to claim 25, wherein $R_3$ and $R_4$ are both fluoro.
27. A compound according to claim 26, wherein $R_5$ is methyl.
28. 4,4,5,5-Tetradehydro-15-methyl-16,16-difluoro-PGE$_1$, a compound according to claim 27.
29. 4,4,5,5-Tetradehydro-15-methyl-16,16-difluoro-PGE$_1$, methyl ester, a compound according to claim 27.
30. A compound according to claim 26, wherein $R_5$ is hydrogen.
31. 4,4,5,5-Tetradehydro-16,16-difluoro-PGE$_1$, a compound according to claim 30.
32. 4,4,5,5-Tetradehydro-16,16-difluoro-PGE$_1$, methyl ester, a compound according to claim 30.

* * * * *

UNITED STATES PATENT OFFICE
CERTIFICATE OF CORRECTION

Patent No. 4,013,695　　　　Dated March 22, 1977

Inventor(s) Chiu-Hong Lin

It is certified that error appears in the above-identified patent and that said Letters Patent are hereby corrected as shown below:

Column 2, lines 50-51, "destrorotatory" should read -- dextrorotatory --;

Column 6, line 21, "slutions" should read -- solutions --;

Column 7, line 37, "ov ovulation" should read -- of ovulation --;

Column 8, line 43, "examle," should read -- example, --; line 51, "cite" should read -- site --;

Column 9, line 18, "15α-PGE$_3$," should read -- 15β-PGE$_3$, --; line 25, "No. 3,208,955" should read -- No. 7,208,955 --;

Column 15, line 49, "(2,3-, 2,4-, 2,5-, 2,6-, 3,4-, or 3,5-(" should read -- (2,3-, 2,4-, 2,5-, 2,6-, 3,4-, or 3,5-) --; lines 50-51, "(3-, or 4-(chloro-" should read -- (3-, or 3-)chloro- --;

Column 18, lines 33 and 53 should read -- or --;

Column 37, line 36, "XXVII" should read -- XXVI --;

Column 41, line 57, "LIv" should read -- LIV --;

Column 43, line 19, "compound of" should read -- compound or --;

Column 44, line 33, "LXIII" should read -- LXXII --;

Column 51, lines 51-52, "trans-CH=λCH-)" should read -- trans-CH=CH-) --;

Column 56, line 14, "γ-lactol acid γ lactone" should read -- γ-lactol --;

Column 64, line 6, "1.13.1, 2.46," should read -- 1.1-3.1, 2.46 --;

Column 65, line 65, "PGF$_2$ , methyl ester" should read -- PGF$_{2α}$, methyl ester --;

UNITED STATES PATENT OFFICE
CERTIFICATE OF CORRECTION

Patent No. 4,013,695      Dated March 22, 1977

Inventor(s) Chiu-Hong Lin

It is certified that error appears in the above-identified patent and that said Letters Patent are hereby corrected as shown below:

Column 70, line 43, "$CH_2-CH_2-CH_2\ C-(CH_2)_g-CH_2-COOR_1$" should read -- $CH_2-CH_2-C{\equiv}C-(CH_2)_g-COOR_1$ --;

Column 70, line 62, "$CH_2-CH_2-C{\equiv}C-(CH_2)_g-2-COOR_1$" should read -- $CH_2-CH_2-C{\equiv}C-(CH_2)_g-COOR_1$ --;

Column 74, line 47, "$PGF_1\alpha_1\alpha$-type" should read -- $PGF_1\alpha$-type --;

Column 75, line 25, that portion of the formula reading

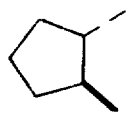    should read    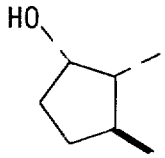

Column 76, line 30, "4GB-" should read -- 4,4,5,5- --.

Signed and Sealed this

Twenty-fifth Day of November 1980

[SEAL]

Attest:

SIDNEY A. DIAMOND

Attesting Officer     Commissioner of Patents and Trademarks